(12) United States Patent
Lye et al.

(10) Patent No.: US 7,687,245 B2
(45) Date of Patent: *Mar. 30, 2010

(54) MICROBIAL DETECTION AND QUANTIFICATION

(75) Inventors: Jason Lye, Atlanta, GA (US); John Gavin MacDonald, Decatur, GA (US); Ning Wei, Roswell, GA (US); Stephanie Martin, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 176 days.

This patent is subject to a terminal disclaimer.

(21) Appl. No.: 10/581,404

(22) PCT Filed: Dec. 16, 2004

(86) PCT No.: PCT/US2004/042461

§ 371 (c)(1),
(2), (4) Date: Jun. 11, 2007

(87) PCT Pub. No.: WO2005/059162

PCT Pub. Date: Jun. 30, 2005

(65) Prior Publication Data

US 2007/0249012 A1     Oct. 25, 2007

Related U.S. Application Data

(63) Continuation-in-part of application No. 10/737,574, filed on Dec. 16, 2003, now Pat. No. 7,282,349.

(51) Int. Cl.
C12Q 1/22       (2006.01)

(52) U.S. Cl. .................. 435/31; 8/400; 436/1

(58) Field of Classification Search .......... None
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,496,066 A * | 2/1970 | Dold et al. ............. | 435/34 |
| 3,502,763 A | 3/1970 | Hartmann | |
| 3,542,615 A | 11/1970 | Dobo et al. | |
| 3,692,618 A | 9/1972 | Dorschner et al. | |
| 3,705,032 A | 12/1972 | Honjo et al. | |
| 3,802,817 A | 4/1974 | Matsuki et al. | |
| 3,849,241 A | 11/1974 | Butin et al. | |
| 4,100,324 A | 7/1978 | Anderson et al. | |
| 4,310,928 A | 1/1982 | Joung | |
| 4,340,395 A | 7/1982 | Magers et al. | |
| 4,340,563 A | 7/1982 | Appel et al. | |
| 4,375,448 A | 3/1983 | Appel et al. | |
| 4,494,278 A | 1/1985 | Kroyer et al. | |
| 4,511,488 A | 4/1985 | Matta | |
| 4,556,636 A | 12/1985 | Belly et al. | |
| 4,640,810 A | 2/1987 | Laursen et al. | |
| 4,677,076 A | 6/1987 | Langhals | |
| 4,775,582 A | 10/1988 | Abba et al. | |
| 4,780,422 A | 10/1988 | Mitani et al. | |
| 4,818,464 A | 4/1989 | Lau | |
| 4,833,003 A | 5/1989 | Win et al. | |
| 4,853,281 A | 8/1989 | Win et al. | |
| 5,036,000 A | 7/1991 | Palmer et al. | |
| 5,112,900 A | 5/1992 | Buddenhagen et al. | |
| 5,407,715 A | 4/1995 | Buddenhagen et al. | |
| 5,464,739 A | 11/1995 | Johnson et al. | |
| 5,468,469 A | 11/1995 | Aszalos et al. | |
| 5,527,171 A | 6/1996 | Soerensen | |
| 5,534,416 A | 7/1996 | Millard et al. | |
| 5,742,943 A | 4/1998 | Chen | |
| 5,744,321 A | 4/1998 | Harewood | |
| 5,792,531 A | 8/1998 | Littleton et al. | |
| 5,900,452 A | 5/1999 | Plamthottam | |
| 5,958,673 A * | 9/1999 | LaClair ................. | 435/4 |
| 6,090,541 A | 7/2000 | Wicks et al. | |
| 6,168,655 B1 | 1/2001 | Nohr et al. | |
| 6,270,724 B1 | 8/2001 | Woodaman | |
| 6,288,159 B1 | 9/2001 | Plamthottam | |
| 6,306,514 B1 | 10/2001 | Weikel et al. | |
| 6,362,006 B1 | 3/2002 | Potyrailo et al. | |

(Continued)

FOREIGN PATENT DOCUMENTS

EP          0266196 A2     5/1988

(Continued)

OTHER PUBLICATIONS

Abstract of Japanese Patent No. JP11083849.

(Continued)

*Primary Examiner*—Lisa J Hobbs
(74) *Attorney, Agent, or Firm*—Dority & Manning, P.A.

(57) ABSTRACT

Suitable dyes are used herein to indicate the presence of microbial contamination by spraying them onto surfaces in the form of an aqueous solution. The dye solution may also be allowed to dry, thus producing the dried residue of an aqueous solution. It's believed that these dyes change color in response to a change in polarity of the environment. Since water is a polar solvent and most bacteria are made from non-polar substances, the presence of bacteria changes the polarity of the environment, triggering a change visible by the unaided eye.

17 Claims, 9 Drawing Sheets

U.S. PATENT DOCUMENTS

| | | |
|---|---|---|
| 6,368,558 B1 | 4/2002 | Suslick et al. |
| 6,383,815 B1 | 5/2002 | Potyrailo |
| 6,524,846 B1 | 2/2003 | Robinson, Jr. |
| 7,300,770 B2 | 11/2007 | Martin et al. |
| 7,399,608 B2 | 7/2008 | MacDonald et al. |
| 2003/0119202 A1 | 6/2003 | Kaylor et al. |
| 2003/0143112 A1 | 7/2003 | Suslick et al. |
| 2003/0198573 A1 | 10/2003 | Forood et al. |
| 2005/0130253 A1 | 6/2005 | Lye et al. |
| 2006/0134613 A1 | 6/2006 | Martin et al. |
| 2007/0140971 A1 | 6/2007 | MacDonald et al. |

FOREIGN PATENT DOCUMENTS

| | | | |
|---|---|---|---|
| EP | 0266196 A3 | | 5/1988 |
| EP | 0517050 B1 | | 12/1992 |
| EP | 0846767 A2 | | 6/1998 |
| EP | 0846767 A3 | | 6/1998 |
| GB | 1107790 A | | 3/1968 |
| GB | 2178847 A | | 2/1987 |
| GB | 2178847 A | * | 2/1987 |
| JP | 11083849 A | * | 3/1999 |
| WO | WO9730341 A1 | | 8/1997 |
| WO | WO0233413 A1 | | 4/2002 |
| WO | WO02103356 A1 | | 12/2002 |
| WO | WO2005016230 A2 | | 2/2005 |
| WO | WO2005016230 A3 | | 2/2005 |
| WO | WO2005059162 A2 | | 6/2005 |
| WO | WO2005059162 A3 | | 6/2005 |

OTHER PUBLICATIONS

Abstract of Article—*A $^1$H NMR Investigation Concerning the Insertion of Pyridinium N-Phenoxide Betaines into Micelles*, Plieninger et al., Liebigs Ann. Chem. 1983, pp. 860-875.

Abstract of Article—*Antimicrobial resistance among clinical isolates of Haemophilus influenzae in northern Italy. Collaborative Study on Pediatric Infectious Diseases*, Garlaschi et al., Eur. J. Epidemiol., vol. 9, No. 1, 1993, pp. 64-69.

Abstract of Article—*Detection of adenovirus DNA in clinical samples by SYBR Green real-time polymerase chain reaction assay*, Watanabe et al., Pediatr. Int., vol. 47, No. 3, 2005, pp. 286-291.

Article—*Chloramphenicol treatment for acute infective conjunctivitis in children in primary care: a randomised double-blind placebo-controlled trial*, Rose et al., www.thelancet.com., vol. 366, Jul. 2, 2005, pp. 37-43.

Article—*Colour and Constitution of Organic Molecules*, John Griffiths, Academic Press, 1976, pp. 16-80 and pp. 146-160.

Article—*Development and use of nested polymerase chain reaction (PCR) for the detection of adenovirus from conjunctivitis specimens*, Dalapathy et al., Journal of Clinical Virology 11, 1998, pp. 77-84.

Article—*Investigation of Micelles, Microemulsions, and Phospholipid Bilayers with the Pyridinium N-Phenolbetaine Er(30), a Polarity Probe for Aqueous Interfaces*, Zachariasse et al., J. Phys. Chem., vol. 85, No. 18, Sep. 3, 1981, pp. 2676-2683.

Article—*Nile Red: A Selective Fluorescent Stain for Intracellular Lipid Droplets*, Greenspan et al., The Journal of Cell Biology, vol. 100, Mar. 1985, pp. 965-973.

Article—*Ocular Virulence of Capsule-Deficient Streptococcus pneumoniae in a Rabbit Keratitis Model*, Reed et al., Investigative Ophthalmology & Visual Science, vol. 46, No. 2, Feb. 2005, pp. 604-608.

Article—*Potential Antitumor Phenoxazines*, Motohashi et al., Medicinal Research Reviews, vol. 11, No. 3, May 1991, pp. 239-294.

Article—*Pyridinium N-phenolate betaine dyes as empirical indicators of solvent polarity: Some new findings*, Reichardt, Pure Appl. Chem., vol. 76, No. 10, 2004, pp. 1903-1919.

Article—*Rapid Diagnosis of Adenoviral Keratoconjunctivitis by a Fully Automated Molecular Assay*, Koidl et al., Ophthalmology, vol. 112, No. 9, Sep. 2005, pp. 1521.e1-1521.e8.

Article—*Second order hyperpolarizability of hydroxystilbazolium salts and their betaines—relationship to chemical structure*, Grummt et al., J. Mater. Chem., vol. 9, 1999, pp. 1419-1424.

Article—*Simplifying Collection of Corneal Specimens in Cases of Suspected Bacterial Keratitis*, Kaye et al., Journal of Clinical Microbiology, vol. 41, No. 7, Jul. 2003, pp. 3192-3197.

Article—*Solvent dependent hyperpolarizability of a merocyanine dye*, Levine et al., J. Chem. Phys., vol. 68, No. 11, Jun. 1, 1978, pp. 5042-5045.

Article—*Synthesis and structure-property relationships of amphiphilic acidochromic hydroxystilbazolium dyes*, Lehmann et al., Sensors and Actuators B 38-39, 1997, pp. 229-234.

Article—*The Change in Research for the Therapy of Tumors*, Sedlacek et al., Chimia, vol. 45, No. 10, Oct. 1991, pp. 311-316.

ASTM E 1164-02—*Standard Practice for Obtaining Spectrometric Data for Object-Color Evaluation*, 2002, pp. 1-8.

Chapters 6 and 9-11 from book entitled *Photodynamic Action and Diseases Caused by Light* by Harold Francis Blum, American Chemical Society Series of Scientific and Technologic Monographs, 1941.

*Colorimetry*, 2$^{nd}$ Edition, International Commission on Illumination, No. 15.2, 1986, 88 pages.

ISO 7724/1-1984 (E)—*Paints and varnishes—Colorimetry—Part 1: Principles*, Oct. 1, 1984, 8 pages.

Japanese Industrial Standard—JIS Z 8722:2000 (E)—*Methods of colour measurement—Reflecting and transmitting objects*, 63 pages.

*Pocket Guide to Digital Printing*, Frank Cost, Delmar Publishers, ISBN: 0-8273-7592-1, pp. 144-145.

Article—*Flow Cytometry and Cell Sorting of Heterogeneous Microbial Populations: the Importance of Single-Cell Analyses*, Davey et al., Microbiological Reviews, Dec. 1996, pp. 641-696.

Article—*Rapid flow cytometry—Nile red assessment of PHA cellular content and heterogeneity in cultures of Pseudomonas aeruginosa 47T2 (NCIB 40044) grown in waste frying oil*, Vidal-Mas et al., Antonie van Leeuwenhoek 80, 2001, pp. 57-63.

Article—*Solvatochromic Dyes as Solvent Polarity Indicators*, Christian Reichardt, Chemical Reviews, vol. 94, No. 8, 1994, pp. 2319-2358.

* cited by examiner

Bacterial Cell Shapes

Round or Cocci     Rod or Baccilli     Spiral or Spirilli

Comma or Vibrios

Filamento

Bacterial Cell Arrangements

Diplococci     Streptococci     Staphylococci

R=CH3- , CH3(CH2)4CH2- , CH3(CH2)10CH2- , CH3(CH2)20CH2-

7.7g(0.083mole)   12.9g(0.09mole)

Theo. 19.6g
Act.  18.6g(crude)

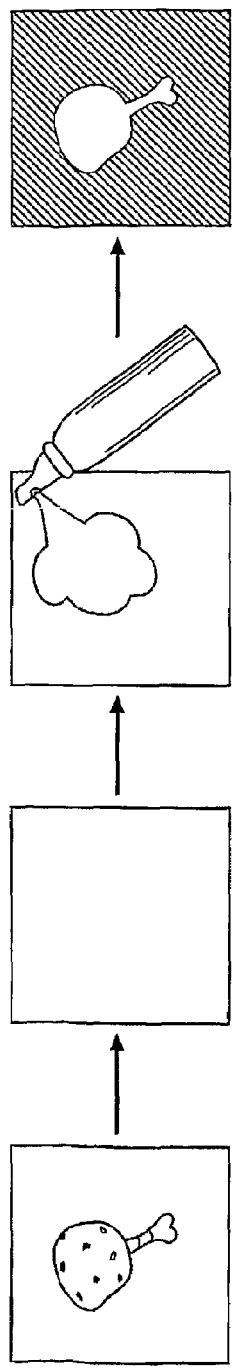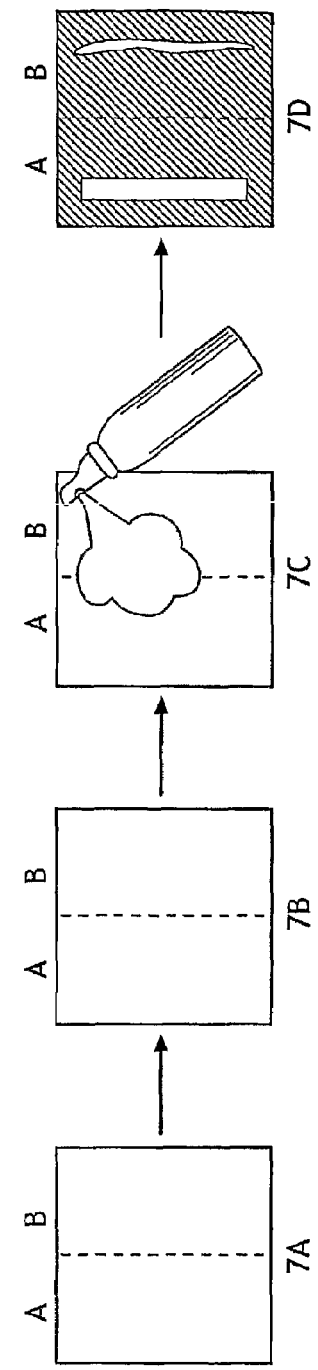
FIG. 6
FIG. 7

13C

13B

13A

MICROBIAL DETECTION AND QUANTIFICATION

This is a Continuation-In-Part of co-assigned U.S. patent application Ser. No. 10/737,674, filed Dec. 16, 2003 now U.S. Pat. No. 7,282,349 and claims the benefit of filing thereof.

BACKGROUND OF THE INVENTION

The invention concerns processes and products for the detection of microbes like bacteria, yeast, mold and viruses.

In our everyday life we are unknowingly exposed to microbial-contaminated surfaces which can lead to illness. Studies have shown specific bacteria-contaminated "hot spots" to include public telephone, door handles, toys in doctors waiting rooms and child care facilities, hot air dryers to dry hands, towels and sponges used in the kitchen, the hands of hospital staff during routine patient care and cross contamination from food preparation surfaces and knives where raw meats and vegetables are mixed.

Recent bacterial contamination outbreaks in various locations in the United States alone have resulted in the death of children and senior citizens and sickening of others. Microbial contamination of food is also a major problem throughout the world. *Salmonella*, *E. coli* and other food-borne bacteria cause untold numbers of illness each year. Acute symptoms include nausea, vomiting, abdominal cramps, diarrhea, fever and headache. Chronic consequences may follow after the onset of acute symptoms. As cross-contamination of surfaces can cause transfer of bacteria from meat, fish, and poultry to uncooked food such as vegetables, the ability to easily detect the presence of bacteria on food-preparation surfaces would be of great benefit.

Similarly, the detection of harmful levels of microbes in the food processing business is very important in maintaining the health of families and customers alike. In the food processing industry, bacteria monitoring is critical. The processing of virtually all foods, from meat packing to cheese production, involves monitoring microbes levels in order to ensure the safety of the food supply.

The havoc wreaked by microbial contamination is not limited to the food industry alone. Recent decades have seen a dramatic rise in "superbugs," a problem whose epicenter exists in the hospital and healthcare community. The overuse of antibiotics as well as inadequacies in hospital cleaning have given rise to methicillin-resistant *S. aureus* (MRSA) and *Clostridium difficile*, as well as vancomycin-resistant enterococci and other gram-negative bacilli (Dancer, 2004). A recent BBC report cited that MRSA claims an estimated 5000 lives yearly. The is article goes on to declare that "Cleanliness remains a major patient concern and MRSA is a growing problem." When one considers that many patients in hospitals are already immuno-compromised and therefore at greater risk of infection, the threat posed by nefarious bacteria in the hospital environment becomes even more menacing.

There are numerous reports and studies dedicated to the topic of hospital cleanliness and the prevention of nosocomial infection.

Similarly, molds such as ergot have been known to grow in certain cereals such as rye and may be potentially hazardous by dint of their production of toxic alkaloids similar to lysergic acid. *Aspergillus niger* and other molds have been known to produce spores that may cause allergic reactions as well as aggravate respiratory conditions such as asthma. *A. niger* may be particularly problematic if it begins to grow on a damp wall, or in air conditioning equipment in the home or commercial buildings.

Certain yeasts, such as *Candida albicans*, can represent another troublesome class of microorganisms. *C. ablicans* has been associated with diaper rash in infants, oral thrush in children and immuno-compromised adults, and vaginal yeast infections. Yeasts may also infect the pharageal region of the body, as well as the gastro-intestinal tract.

Current methods of bacteria detection involve sampling the surfaces of equipment. In a food processing environment, the equipment could be meat cutting machinery, whereas in a food preparing environment such as a restaurant or in the home, the surface could be a table, a cutting board, the inside of a refrigerator, or a work surface. The sample is then incubated overnight to growth a culture. The overnight growth culture allows the sample to grow on an agar plate at appropriate temperature and humidity so that the bacteria grow and multiply until they form colonies large enough to be visible to the naked eye. After incubating for the prescribed time and allowing the bacteria colonies to grow, the agar plate sample is examined manually and the colony forming units (CFU) estimated by a trained technician. This method is somewhat expensive and involves a substantial time lag; a time lag in which contaminated product may have been shipped or people exposed to microbes present.

It is clear that there exists a need for a process and product which allows for the rapid detection of harmful microorganisms.

SUMMARY OF THE INVENTION

In response to the foregoing difficulties encountered by those of skill in the art, we have developed an indicating composition that has a mobile phase and a microbe sensitive colorant that undergoes a visibly detectable change in the presence of microbes. The composition may be applied to surfaces to reveal the presence of the microbes. The mobile phase may be a disinfectant. The colorant provides a color change that is visible to the unaided eye in the presence of microbes. The mobile phase may be a liquid or gel and the colorant may be a dye. In some embodiments, the colorant changes color at a rate proportional to the concentration of microbes. In other embodiments, the amount of microbe present is proportional to a quantity of colorant that undergoes a change.

Examples of suitable dyes include merocyanine dyes, 4-[2-N-substituted-1,4-hydropyridin-4-ylidine)ethylidene]cyclohexa-2,5-dien-1-one, red pyrazolone dyes, azomethine dyes, indoaniline dyes, diazamerocyanine dyes, zwitterionic dyes as exemplified by Reichart's dye, and others as well as mixtures thereof. Of particular suitability are dyes that are zwitterionic, wherein the zwitterion is contained within a contiguous $\pi$ electron system comprising the dye chromogen. An additional class of dyes that appear to be especially useful for microbe indicators are merocyanine dyes.

The dye may also be applied to a surface as solvent-based or water based solution and allowed to dry, leaving the dried residue of the applied dye solution. The dried residue will change color upon contact with microbes and so may be used on packaging like facial tissue boxes, on medical paraphernalia such as gloves, and on other surfaces which may be prepared with the dye before the material is used, and which will subsequently indicate microbial contamination. Surprisingly, the inventors found that when these dyes are applied to a surface and allowed to dry, both the solvent used to make the coating and the use of additives such as hydroxypropyl-beta-cyclodextrin and surfactants had a significant impact on the microbe detecting ability of the coating.

Hydroxypropyl-beta-cyclodextrin has been found to be effective in enhancing the brightness of the colorant after it is has been coated onto a paper towel or similar wipe material. While not wishing to be bound by theory, we believe that the color of the dyes is improved by the addition of a cyclodextrin derivative by inhibiting the crystallization of the dye. Other chemicals may be added to a wipe to help prevent false positive readings due to the presence of bleach, which has been found to interfere with the dye.

Lateral flow devices incorporating microbe indicating colorants are also included within the teachings of the invention. These devices have a membrane having detection and control zones, where the detection zone changes color in response to the presence of bacteria and the control zone remains the original dye color to indicate that the assay is functioning properly.

Also described herein is a method for the detection of microbes on surfaces by applying a solution containing a microbe-sensitive colorant to a surface and observing a visually detectable change indicating the presence of microbes.

BRIEF DESCRIPTION OF THE DRAWINGS

FIGS. 6A-D are diagrams of the indication of microbial contamination using aged chicken.
FIGS. 7A-G are diagrams of a side-by-side indication of microbial contamination indication and cleaning.

DETAILED DESCRIPTION OF THE INVENTION

The present invention involves the detection of bacteria and other microorganisms and the use of the term "microbe" herein should be understood to include bacteria, fungi like yeasts and molds, and viruses.

There are thousands of different kinds of bacteria. Some differ only slightly and it takes a highly trained person to identify them. There are also groups which differ greatly in growth habits and appearance and are quite easily identified. Regardless of minor differences, most bacteria can be classified according to the five basic cell shapes illustrated in FIG. 1. From left to right in FIG. 1 the shapes are round or cocci, rod or bacilli, spiral or spirilli, comma or vibrios, and filaments.

Figure 2:
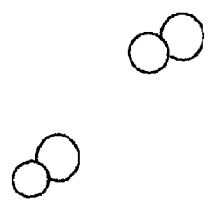
FIG. 2 is a drawing of bacterial cell arrangements.
Figure 2:
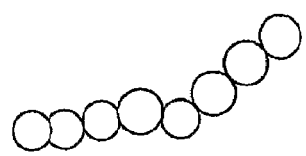
Figure 2:
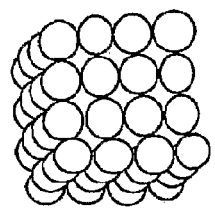

In addition to their different shapes, their cell arrangement varies from diplococci, streptococci, and staphylococci (left to right in FIG. 2). For example, some cocci are always grouped in pairs (diplococci). Others are arranged in chains (streptococci). Still others are bunched (staphylococci). Diplococci are the known to cause pneumonia. Streptococci are often associated with "strep throat." Staphylococci are familiar to many because of their role in "staph infections" and some types of food poisoning.

Bacteria also vary somewhat in size, but average about $1/25,000$ inch (2.54 cm) per bacteria. In other words, 25,000 bacteria laid side by side would occupy only one linear inch. One cubic inch is big enough to hold nine trillion average-sized bacteria—about 3,000 bacteria for every person on earth.

While there is great discussion on the theoretical basis of the subdivision of bacteria based on modern molecular biological concepts, for the working microbiologist a rapid means of subdivision is on the basis of the Gram reaction (a staining method to classify bacteria) and morphology.

The gram-positive bacteria retain crystal violet stain in the presence of alcohol or acetone. They include the important genera: *Actinomyces, Bacillus, Bifidobacterium, Cellulomonas, Clostridium, Corynebacteriumk, Micrococcus, Mycobacterium, Nocardia, Staphylococcus, Streptococcus* and *Streptomyces*. Some of the Gram-positive bacteria notably those of the genera *Corynebacterium, Mycobacterium* and *Nocardia* retain dyes even in the presence of acid. These are known as Acid-Fast bacteria.

The gram-negative bacteria do not retain crystal violet stain in the presence of alcohol or acetone. They include the important genera: *Acetobacter, Agrobacterium, Alcaligenes, Bordetella, Brucella, Campylobacter, Caulobacter, Enterobacter, Erwinia, Escherichia, Helicobacterium, Legionella, Nesseria, Nitrobact, Pasteurelia, Pseudomonas, Rhizobium, Rickettsia, Salmonella, Shigella, Thiobacilus, Veiellonealla, Vibrio, Xanthomonas* and *Yersinia*.

Bacteria membranes generally are made of lipid bi-layers of liposaccharides. There are differences between gram-negative and gram-positive bacteria cell membranes, i.e, cell walls. The cell wall of gram-negative bacteria is a thinner structure with distinct layers. There is an outer layer which is more like a cytoplasmic membrane in composition with the typical trilaminar structure.

The main component of the gram-negative cell wall is lipopolysaccharide. Additionally there is present phospholipid, protein, lipoprotein and a small amount of peptidoglycan. The lipopolysaccharide consists of a core region to which are attached repeating units of polysaccharide moieties. A component of the cell wall of most gram-negative bacteria is associated with endotoxic activity, with which are associated the pyrogenic effects of gram-negative infections. On the side-chains are carried the bases for the somatic antigen specificity of these organisms. The chemical composition of these side chains both with respect to components as well as arrangement of the different sugars determines the nature of the somatic or O antigen determinants, which are such important means of serologically classifying many gram-negative species. In many cases it has been shown that the reason for certain organisms belonging to quite different species, giving strong serological cross-reactivity is due to their having chemically similar carbohydrate moieties as part of their lipopolysaccharide side chains, which generally have about 30 repeating units.

Gram-positive bacteria are characterized by having as part of their cell wall structure peptidoglycan as well as polysaccharides and/or teichoic acids. The peptidoglycans which are sometimes also called murein are heteropolymers of glycan strands, which are cross-linked through short peptides.

The bases of the murein are chains of alternating residues of N-acetylglucosamine and N-acetyl muramic acid which are Beta-1,4-linked. The muramic acid is a unique substance associated with bacterial cell walls. These chains are cross-linked by short polypetide chains consisting of both L- and D-amino acids. While in gram-negative bacteria the peptidoglycan is simple in structure and comparatively uniform throughout most genera, in gram-positive bacteria there is a very big variation in structure and composition. In general the peptidoglycan is multilayered. There have also been recorded some minor variations in composition in some groups. Thus, in *Mycobacterium* and *Nocardia* the N-acetyl moiety of the muramic acid is replaced by the oxidized form N-glycolyl. The amino acid composition of the both the cross-linking as well the stem polypeptides can vary extensively with different groups. These differences form the basis for the taxonomy of these organisms.

Molds and yeasts are organisms belonging the Fungi kingdom. Although many molds, and fungi are helpful to humans, several are pathogenic and can release harmful mycotoxins which may result in poisoning or death. Yeasts can also lead to infection, the most widely known probably being yeast vaginitis.

Zygomycota is a class of fungi which includes black bread mold and other molds exhibiting a symbiotic relationship with plants and animals. These molds are capable of fusing and forming tough "zygospores." Ascomycota is a class of fungi, which includes yeasts, powdery mildews, black and blue-green molds, and some species which cause diseases such as Dutch elm disease, apple scab, and ergot. The life cycle of these fungi combines both sexual and asexual reproduction and the hyphae are subdivided into porous walls which allow for passage of the nuclei and cytoplasm. Deuteromycota is another class of fungi which includes a miscellaneous collection of fungi that don't easily fit into the aforementioned classes or the Basidiomycota class (which includes most mushrooms, pore fungi, and puffball fungi). These deuteromycetes include the species that create cheese and penicillin, but also includes disease-causing members such as those that lead to athlete's foot and ringworm.

The use of dyes in the biomedical area has seen a remarkable growth in research interest and technical importance in the recent years. Dyes are used, for example, in many areas of analytical biochemistry, medical diagnostics and even in the treatment and prevention of disease. The color of the dye is essential for certain applications and range from simple organic reactions for spectroscopic detection (U.S. Pat. No. 5,036,000) and measurement of body fluid analytes (European Patent No. 0 250 700) to high definition imaging technology for tumor detection (Motohashi, Med. Res. Rev., 11, 239, 1991). Dyes can also be used clinically for the treatment of disease (U.S. Pat. No. 5,468,469). Photodynamic therapy (Sedlacek, "The change in research for the therapy of tumors", Chimia, 45, 52, 1991) is successfully used in the treatment of certain kinds of cancer; such as malignancies of the skin, head, neck, lung and esophagus. Other therapeutic applications are associated with the antiviral and bactericidal properties of dyes. Dyes are also the key agent in the important areas of histology, fluorescent biolabeling and fluorescent bioprobes. The techniques involved are highly sophisticated and require staining, washing and cross staining (Blum, Photodynamic action and disease caused by light" Reinhold, New York, 3, 1941).

The inventors have found that a microbe-indicating spray as well as a rapid method for microbe quantification may be made using particular colorants. Potential applications of this technology include but are not limited to detection of microbes on solid surfaces such as counter-tops, hands, medical areas, bathrooms, bedrails, medical equipment, surgery tables, utensils, kitchens, food, food preparation surfaces, food processing equipment, door knobs, phones and computer key-boards. This colored dye coating, spray, or solution is sensitive to harmful levels of bacteria and other microorganisms and the color change serves as a visual indicator tool to verify if cleaning and/or decontamination of the surface was effective.

The requirements for an indicating technology are fairly rigorous as the dye used must be sensitive to both gram-positive and gram-negative bacteria strains. The dye should rapidly interact with the microbe or a microbial metabolite. For maximum versatility, the dye should also be sensitive to other microorganisms, such as yeast and mold.

As mentioned earlier, dyes have been used for some time as stains for both cell and bacteria identification. The stain solution reacts or is preferentially retained by the cell or bacteria to help identify by improving the contrast between it and the background or other components present (Johnson, 1995). Usually, a stain has to be applied to a surface, then the excess removed by either shaking, or rinsing in order to highlight the presence of microbes. The inventors are unaware of any previous reports of a colorant that changes color upon exposure to or upon interaction with microbes.

Solvatochromism may be responsible for the color changes seen, however the inventors do not wish to be bound by one particular theory. Solvatochromic dyes undergo a color change when the molecular environment, such as solvent polarity and/or hydrogen bonding propensity, changes. A dye may be blue in color in a polar environment such as water, for example, but may be yellow or red in a non-polar environment such as a lipid-rich solution. The colors produced by such "suitable dyes" depend on the molecular polarity difference between the ground and excited state of the dye as discussed more fully below. Reichardt's dye was selected as a model dye for investigation.

The inventors wondered if certain solvatochromic dyes might be useful to detect microbes by responding to the differences in polarity between certain cell components (such as the cell membrane, the cytoplasm, etc.) and the polarity outside of the cell. The inventors found that when microbes were contacted with certain of these dyes coated onto substrates such as paper towels, a color change was indeed observed—not only was there a color change, but in most cases the dye was decolorized in the region contacted by the bacteria. To the surprise of the inventors, further research suggested that the mechanism may not be entirely attributed to solvatochromism. In fact, the inventors report here that, to their surprise, they found the following:

i) The quantity of the dye decolorized by bacteria or other microbes may be correlated to the concentration of microorganisms exposed to the dye, suggesting that the method was quantitative vs. qualitative, and ii) a range of microorganisms could be detected including gram positive and gram negative bacteria, yeast, and mold, and iii) the dyes tested could be used as a dry film coating or as a solution added to a liquid containing bacteria, or as a spray-on detector system, and, iv) when used as a dry coating on, for instance, a paper towel or an enamel surface, the properties of the solvent from which such dyes were applied significantly impacted the performance (decolorizing time, contrast between decolorized and non-decolorized areas, and sensitivity) of the detecting dye, and, v) when used as a dry coating on, for instance, a paper towel, additives included in the coating with the dye may impact the performance (decolorizing time, contrast between decolorized and non-decolorized areas, and sensitivity) of the detecting dye. For instance, hydroxypropyl-beta-cyclodextrin enhances the performance of the detecting dye, and, vi) the bacteria induced decolorization of these dyes may be reversed using a strong base.

While solvatochromism could contribute to the color changes observed, these observations may also be consistent with other plausible mechanisms. For instance, these observations may also be consistent with an acid—base interaction of some type, or a proton donation reaction of some type that may contribute to color changes in the dye caused by the presence of bacteria. The inventors have also not entirely ruled out the possibility that a redox type reaction may also be contributing to the perceived changes in color when certain dyes are exposed to a range of microorganisms. Other factors could also contribute to the color changes observed with certain dyes in the presence of microbe, for instance, there may be an interaction with a portion of the cell membranes with certain dyes that leads to color changes. Yet another possibility is that the highly organized acid moieties on the bacteria cell walls may be able to protonate certain indicator dyes, resulting in a loss of color.

The inventors have discovered a surprising and as yet unexplained phenomenon and used it to develop a method useful for the detection and quantification of a variety of microorganisms.

Generally, regarding visual detection of color changes; "color" is a type of sensation that arises when the machinery of the human eye detects the presence or absence of light of various wavelengths reflected or emitted from objects in the visual field. Light entering the eye is subjected to a spectral analysis by three types of retinal cone cells that are sensitive to specific regions of the visible spectrum. Stimuli from these cells are in turn processed by retinal neurons, optic nerve neurons and the visual cortex such that a sensation of color is experienced. While several mechanisms exist to impart color (for instance, absorption, emission, fluorescence, phosphorescence, refraction, diffraction, etc.) the suitable focus is limited to absorptive color. In other words, this invention relates to dyes that owe their color to absorbing certain wavelengths of light.

Because of the way in which the human eye functions, the color perceived is usually the complement of the color associated with the wavelength of light being absorbed by the object. An object that appears to be red in color when viewed in white light, for example, is in fact selectively absorbing bluish light in the range of 490 to 500 nm wavelength. Similarly, an object that appears yellow in white light is in fact absorbing blue light in the range of 435 to 480 nm.

Absorption of visible light by molecules is associated with electronic transitions within the molecule and results in the generation of an excited state. The energy difference between the ground state of the molecule and the relevant excited state determines the wavelength of the light absorbed according to the Planck relationship:

$$E = h\nu$$

Where $E$=energy, $h$=Planck's constant, $\nu$ is the frequency of the photon of light absorbed, and is related to wavelength $\lambda$ and the speed of light $c$ by:

$$\nu = c/\lambda$$

A state diagram may be used to depict electronic transitions graphically:

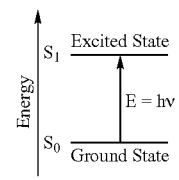

Clearly, the energy of the photon absorbed is inversely proportional to the wavelength of the photon. Thus, photons of blue light (435-480 nm) have higher energy than yellow light (580-595 nm). The color of a dye in solution or on an object when viewed under white light, therefore, is determined by the transition energy between the ground state of the dye molecule and the first allowed excited state.

The light absorbing portion of a dye is conventionally known as the chromogen of the dye. The chromogen comprises a chromophore connected to a conjugated system. The chromophore is the group principally giving rise to the color of a dye, for instance, an azo group as in the case of azo dyes, a polyene group, as in the case of carotene, carbonyl groups, as in anthraquinone and merocyanine dyes. There are many other chromophores. Auxochromes influence the color and intensity of a dye by acting upon the conjugated chromogen. Auxochromes may or may not be conjugated with the chromogen. For instance, an amino group conjugated to an azo group (chromophore) via, for instance, a benzene ring, will form an aminoazo chromogen. The conjugated amino auxochrome shifts the absorption band of the azo group to longer wavelengths and increases the intensity of the absorption band. However, judicious placement of a sulfonic acid group to an amino azo chromogen is not conjugated, however, the electron withdrawing effect causes a shift of absorption to longer wavelengths.

An example of a dye that has a ground state more polar than the excited state is the merocyanine dye 1 as shown below. The charge-separated left hand canonical 1 is a major contributor to the ground state whereas the right hand canonical 1' is a major contributor to the first excited state.

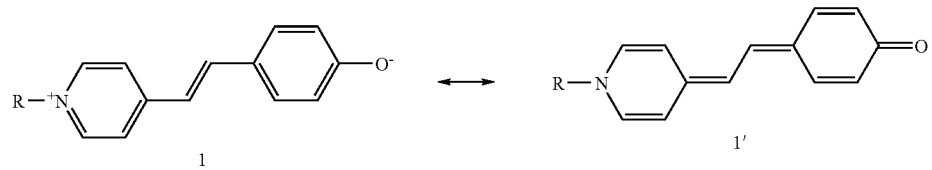

Indigo 2, as shown below, is an example of a dye that has a ground state that is significantly less polar than the excited state. The left hand canonical form 2 is a major contributor to the ground state of the dye, whereas the right hand canonical 2' is a major contributor to the excited state.

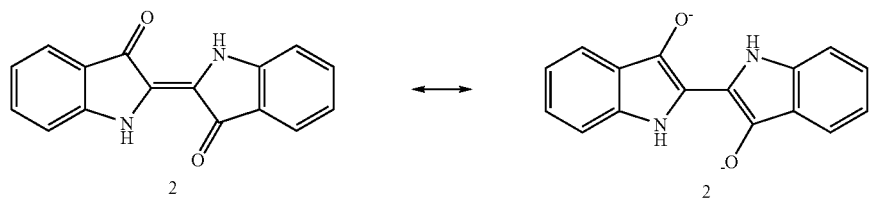

Suitable dyes for the practice of this inventions include those discussed above as well as Reichardt's dye, merocyanine dyes, zwitterionic dyes in which the formal positive and negative charges are contained within a contiguous π-electron system, 4-[2-N-substituted-1,4-hydropyridin-4-ylidine) ethylidene]cyclohexa-2,5-dien-1-one, red pyrazolone dyes, azomethine dyes, indoaniline dyes, diazamerocyanine dyes, and mixtures thereof. Merocyanine dyes fall within the donor—simple acceptor chromogen classification of Griffiths as discussed in "Colour and Constitution of Organic Molecules"Academic Press (London) 1976, wherein a carbonyl group acts as an electron acceptor moiety. The electron acceptor is conjugated to an electron donating group, for instance, an hydroxyl or an amino group that is able to donate electrons. Merocyanine dyes are a relatively broad class of dyes that includes structure 3, wherein a nitrogen atom contained in a heterocyclic system serves as a donor. n may take any integer value including 0. Merocyanine dyes have a charge separated (zwitterionic) resonance form.

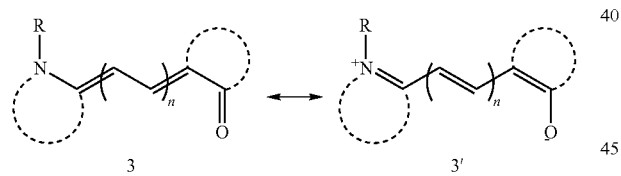

Acyclic merocyanine dyes are also known, including vinylalogous amides. Merocyanine dyes have been studied for their ability to photosensitive silver halide to certain wavelengths of light for use in photographic film. Many merocyanine dye structures are known. Structures 4-14 show several non-limiting examples of merocyanine dyes. Note that for each of these dyes, a charge separated resonance structure may be drawn. The literature suggests that the charge separated (zwitterionic) form contributes significantly to the ground state of the dye.

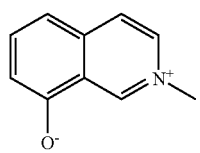

4

-continued

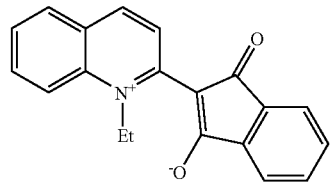

5

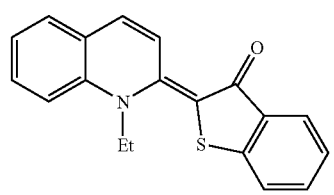

6

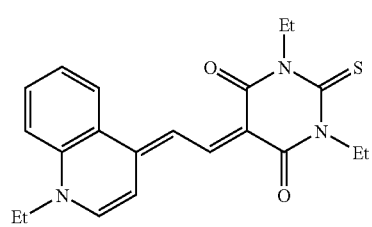

7

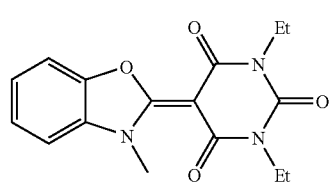

8

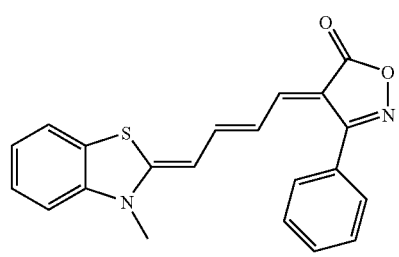

9

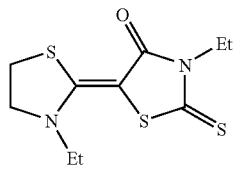

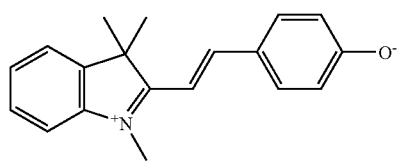

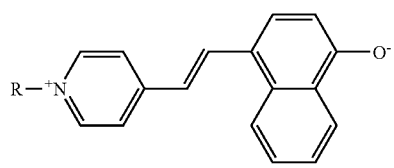

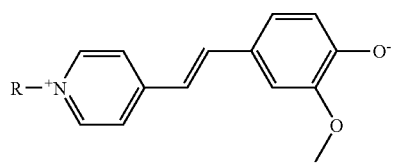

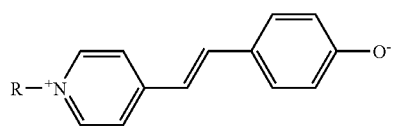

where R may be methyl, alkyl, aryl, phenyl.

Zwitterionic Chromogens

Certain dyes may be prepared that are permanently of a zwitterionic form. That is to say, these dyes have permanent charges associated with the π-electron system and a neutral resonance structure for the chromogen cannot be drawn. Such dyes include Reichardt's dye 15, which conforms to the general structure 16.

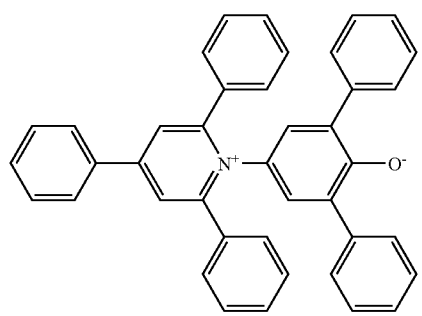

Additional non-limiting structures 17-25 may include the following, which conform to the general structure 16:

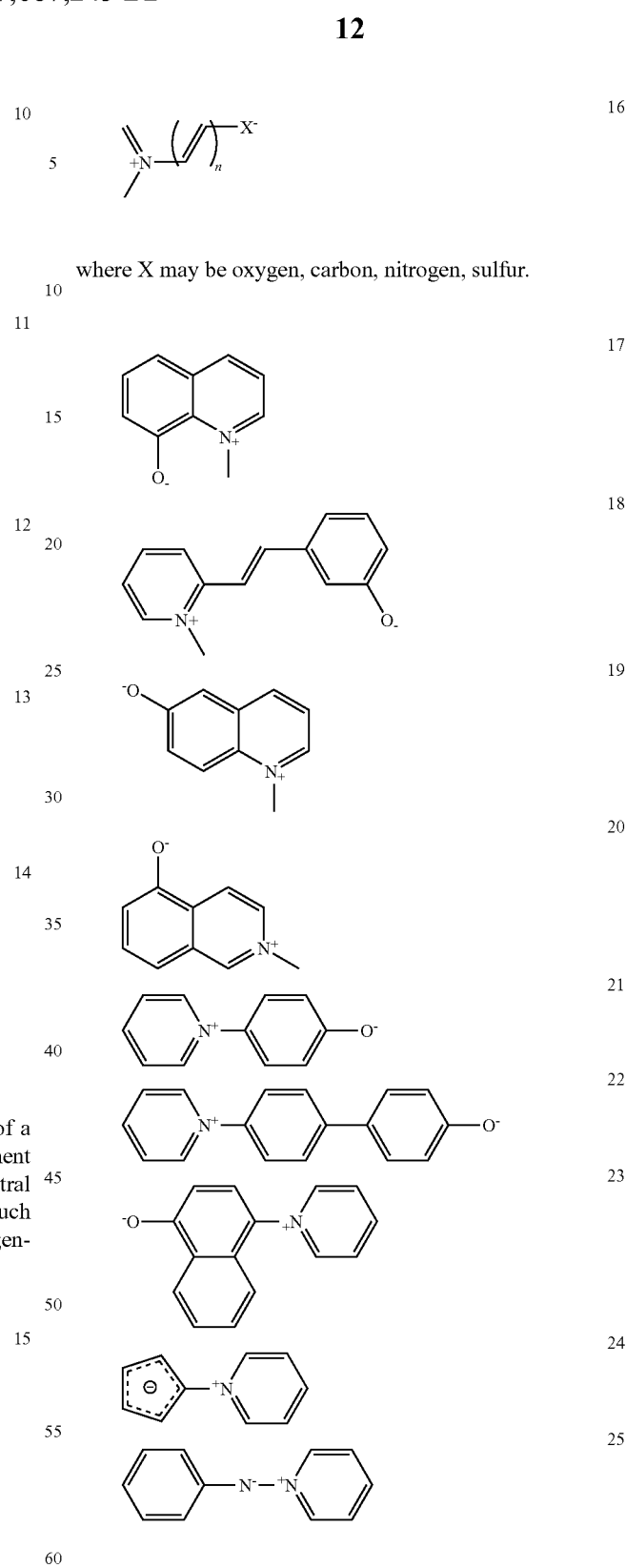

where X may be oxygen, carbon, nitrogen, sulfur.

The amount of dye must be sufficient to allow a change in color upon contact with microbes where the change is detectible to the unaided eye, and so will depend on the sensitivity of the dye. The amount of dye found to be sufficient is generally between 0.01 and 10 weight percent, more desirably between 0.05 and 5 and still more desirably between 0.1 and 3 weight percent on a dry basis. The color change occurs quite rapidly in a manner that is dependent upon the concentration and type of microorganism.

The composition includes the microbe-sensitive colorant as described above, and a mobile phase. The term "mobile phase" includes liquids and gases that may be used as carriers for the colorant. Acetonitrile, isopropanol, and mixtures of xylenes have been found to be suitable carriers, though any effective carrier may be used. The mobile phase may further also be a disinfectant or bactericidal composition.

The colorant dye may be in the form of a liquid that may be sprayed or wiped onto a surface to indicate the presence of microbes. Liquid containing the dye may be applied to surfaces and the applied liquid allowed to dry, forming the dried residue of the dye that may at a later time be exposed to contamination by microbes. Upon exposure to microbes, the dried residue will change color, indicating the presence of microbes. Such a method of indication using the dried residue of a solution applied dye may be useful for use on solid surfaces like, for example, packaging such as facial tissue boxes, stickers, paper, tissues, medical paraphernalia like surgical gloves, surgical gowns and drapes, face masks, head coverings like bouffant caps, surgical caps and hoods, examination and surgical gloves, footwear like shoe coverings, boot covers and slippers, wound dressings, bandages, sterilization wraps, wipers, garments like lab coats, coveralls, aprons and jackets, patient bedding, stretcher and bassinet sheets, food preparation wraps, dish sponges, cloths, door handles, telephones, computer keyboards, computer mice, pens, pencils, notepads, toilet handles, wound dressings, bandages, and toys (e.g. in doctors waiting rooms, daycare facilities).

Substrates onto which the solvatochromic dye may be coated may therefore include wipes, as well as other articles that may be exposed to bacteria like those mentioned above. The solvatochromic dyes may also be incorporated into lotions or cream used to check the hands for microbial contamination. The dye may be incorporated into sponges or dish towels to warn of contamination.

Substrates suitable for use as a wipe for coating with colorants include any of those traditionally used for wipes including films, woven and nonwoven fabrics, cellulosic substrates like tissues, paper towels and coform materials, airlaid materials, bonded-carded webs and so forth. Nonexclusive examples of substrates may be found in U.S. Pat. Nos. 4,775,582 and 4,853,281, 4,833,003, and 4,511,488, all assigned to the Kimberly-Clark Corporation.

A nonwoven fabric may be made according to processes like spunbonding, meltblowing, airlaying, bonding and carding, and so forth. Nonwoven fabrics may be made from thermoplastic resins including, but not limited to polyesters, nylons, and polyolefins. Olefins include ethylene, propylene, butylenes, isoprene and so forth, as well as combinations thereof.

"Spunbonded fibers" are small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more desirably, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, natural polymers (for example, rayon or cotton fibers or other cellulosic materials) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

A bonded carded web is made from staple fibers which are sent through a combing or carding unit, which breaks apart and aligns the staple fibers in the machine direction to form a generally machine direction-oriented fibrous nonwoven web. Once the web is formed, it then is bonded by one or more of several methods such as powder bonding, pattern bonding, through air bonding and ultrasonic bonding.

In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another. Examples of airlaid teachings include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

The inventors have discovered that bleaches used to clean surfaces like, for example, sodium hypochlorite solution, chlorine, and sodium bisulfite could possibly negatively impact solvatochromic dyes and cause a color change even though bacteria is not present. Another aspect of the invention, therefore, includes a bleach detector colorant in a wipe along with solvatochromic dyes. The indicator could be, for example, 2,2',5,5'-tetramethyl benzidine, which is normally colorless and turns red when exposed to chlorine or sodium hypochlorite. The indicator could also be a combination of starch and iodine which turns black in the presence of chlorine or hypochlorite. Yet another indicator, fuchsine, may be useful for detection of sulfites, such as sodium metabisulfite. Fuchsine is pink and changes to colorless when exposed to sulfites. In this way, areas of the wipe may be designated as sensitive to bacteria and other areas as sensitive to bleaches and preservatives so that surfaces containing active bleach give color change combinations that allow the user to distinguish bacteria contamination from bleach. The bleach indicator could be printed in a pattern to spell the word "BLEACH", hidden on the wipe so that if the wipe were passed through bleach, the word BLEACH would become visible, along with any other color change that the bleach may cause to the solvatochromic dye. The amount of bleach indicator need only be an amount sufficient to cause a color change that may be detected by the unaided eye and is in the same range as the solvatochromic dye.

The inventors also believe that it is possible to include small swatches of a) a solvatochromic dye that detects bacteria, b) a chlorine/hypochlorite detector material, such as tetramethyl benzidine, c) an oxidizing agent detector such as a mixture of starch and potassium iodide, d) a bisulfite indicator such as fuschine, e) a nitrite detecting reagent, as examples, onto an indicating strip. In this way, a variety of quality indicators could give a status or quality of, for example, food.

In another aspect of the invention, a coating on the substrate may be used to inhibit the detecting dye(s) from crystallizing, thereby obtaining a coating that has greater sensitivity to microbes. Ideally, a coating that has single dye molecules on the surface would have greater sensitivity for microbes. Each dye molecule would be free to interact with the microbial membrane. In contrast, small crystals of dye first have to dissolve and then penetrate the membrane. While not wishing to be bound by theory, we believe that hydroxypropyl-beta-cyclodextrin, hydroxyethyl-beta-cyclodextrin, gama-cyclodextrin, hydroxypropyl-gama-cyclodextrin, hydroxyethyl-gama-cylodextrin (hereinafter collectively "cyclodextrin"), all available from Cerestar International of Hammond, Ind., USA, hinder the crystallization of the dye, allowing a more vivid dye color to occur on the substrate. The amount of cyclodextrin has been found to be effective is between 0.001 and 2 weight percent, desirably between 0.01 and 1 weight percent and still more desirably between 0.025 and 0.5 weight percent.

Certain surfactants have also been found to assist dyes in detecting microbes. Surfactants include the SURFYNOL® range of surfactants available from Air Products and Chemicals, Allentown, Pa. and TWEEN® 80, a polyoxyethylene available from Fischer Scientific, Pittsburgh, Pa.

Figure 1:
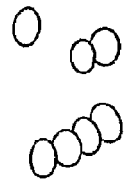
FIG. 1 is a drawing of the five basic bacterial cell shapes.
Figure 1:
Figure 1:
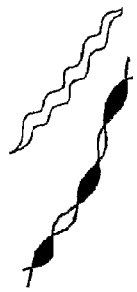
Figure 1:
Figure 1:

Another method of utilizing the detecting dyes to detect bacteria is in the form of a lateral flow detection device. Such devices 2, as shown in FIG. 1, have a deposition pad, membrane, and a wicking pad, (not visible separately) though in some embodiments the deposition pad may be optional. The device 2 has a detection zone 4 and a control zone 6. In use, a liquid sample is deposited on the device 2 in a sample area 8 and flows through the device 2 toward the wicking pad 10, passing through the detection zone 4. Sovatochromic dye is deposited in the detection zone 4, in a line in this case though other shapes could be used, and in the control zone 6, also in a line. As the sample moves through the detection zone 4, if microbes are present, the dye in the detection zone 4 will change color. The dye in the control zone 6 will not change color since the bacteria will be captured in the detection zone 4. The control zone 6 is used to indicate that the assay is running properly. The color of the detection zone 4 can be compared to the color of the control zone 6 to indicate the relative magnitude of the microbes present. More than one solvatochromic dye line may be used since the sensitivity of dyes to different microbes differs. Some dyes, for example, are more sensitive to gram positive bacteria and some are more sensitive to gram negative bacteria. In this way more than one type of bacteria or other microbes may be detected.

The following examples help to illustrate various embodiments of the invention.

EXAMPLE MATERIALS

All reagents and solvents were obtained from Aldrich Chemical Company Inc. (Milwaukee, Wis.) unless otherwise noted and were used without further purification. The microorganisms used in the study were:
1. Gram negative (viable)
*Escherichia coli* (ATCC #8739).
*Psuedomonas aeruginosa* (ATCC #9027)
*Salmonella choleraesuis*
*Gardnerella vaginalis*
2. Gram positive (viable)
*Staphylococcus aureus* (ATCC #6538)
*S. Xylosis*
*Lactobacillus acidophilus*
3. Gram positive (dead)
*Staphylococcus Aureus* (ATCC #6538)
*S. Xylosis.*
4. Yeast (viable)
*Candida Albicans*
5. Mold (viable)
*Aspergillus Niger*

Reichardt's dye (2,6-diphenyl-4-(2,4,6-triphenylpyridinio)-phenolate) and 1-docosyl-4-(4-hydroxstyryl)-pyridinium bromide were purchased from Aldrich Chemical Company of Milwaukee, Wis. The other merocyanines used in this study were synthesized in-house and are described in detail below.

Synthesis of Merocyanine Dyes

1-Decosyl-4-(4-hydroxystyryl)-pyridinium bromide was commercially available from Aldrich Chemical Co. (Milwaukee, Wis.) and used directly.

Additional examples of merocyanine dyes were synthesized in the laboratory in a two-step reaction.

Figure 3:
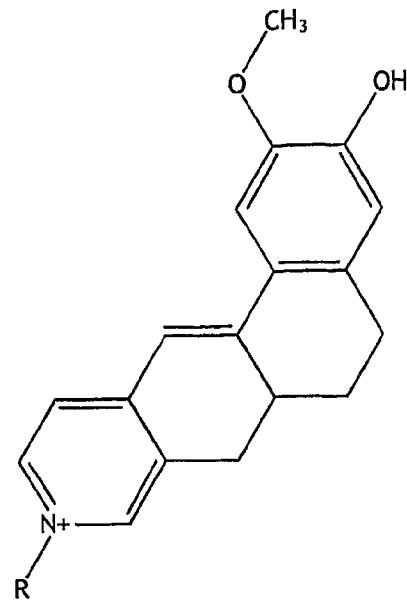
FIG. 3 is a drawing of merocyanine dye synthesis.

The dye synthetically prepared using the synthetic method are shown in FIG. 3.

Figure 4:
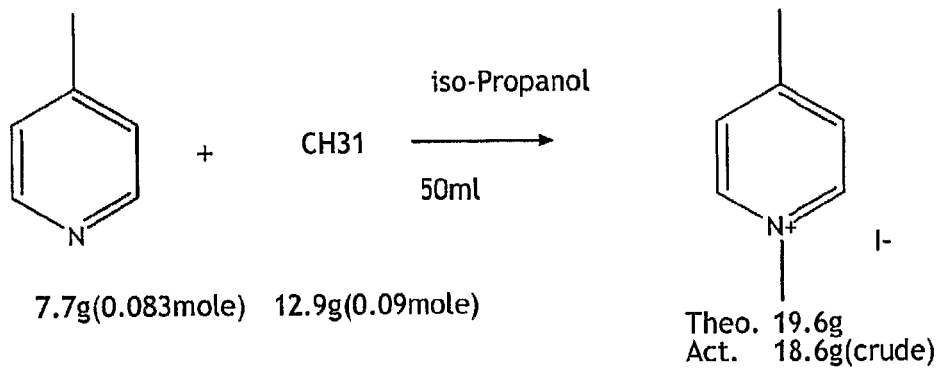
FIG. 4 is a drawing of merocyanine dye synthesis.

Methyl iodide was added slowly to a stirred solution of δ-picoline in 50 ml of isopropanol in an ice-bath as shown in FIG. 4. After addition was complete, the reaction was heated to reflux and reflux continued for 2 hours. The solution was then chilled in an ice-bath and the precipitate filtered, and washed with chilled alcohol, on a Buchner funnel. The powder was then dried in the fume-hood for 2 hours. Yield of crude product was 18.6 grams. The crude product was not further purified and used directly for the next step.

Figure 5:
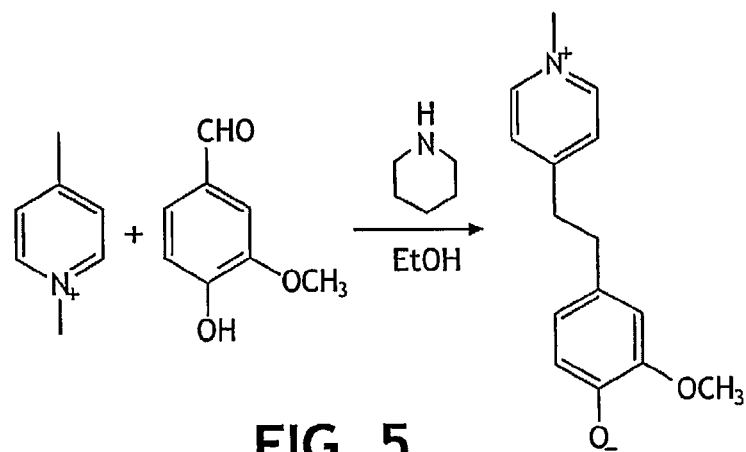
FIG. 5 is a drawing of the methylation of picoline.

N-methyl-δ-Picolone (9.4 g, 0.04 mole), and vanillin (6.1 g, 0.04 mole) were all dissolved into 50 ml of ethanol with stirring as shown in FIG. 5. To this solution was added piperidine (3.4 g, 0.04 mole) and the mixture refluxed for 16 hours. The reaction mixture was then chilled in an ice-bath and the product filtered off using a Buchner funnel and washed with chilled ethanol.

The crude dye of structure 13 above, where R=methyl, was then stirred in 250 ml of 0.2 Molar potassium hydroxide solution for 60 minutes to form the zwitterion and then filtered off using a Buchner funnel. The dye was then crystallized from the minimum quantity of a 1:1 water/methanol mixture. The yield was 9.4 g (98%).

The other dyes were synthesized in a similar manner starting from the respective alkyl iodide. The following Table 1 shows the compounds and the yields obtained for dye structure 13 for three different R groups.

TABLE 1

The alkyl derivatives synthesized and the yields obtained

| ALKYL GROUP | YIELD (%) |
| --- | --- |
| R = METHYL | 98 |
| R = HEXYL | 92 |
| R = DODECYL | 87 |

Example 1

Reichardt's Dye in Acetonitrile Solvent Applied to a Previously Contaminated Surface In order to investigate the use of these dyes as a spray, a solution of Reichardt's dye, (160 mg in 10 mL of acetonitrile) was made. A spray bottle with an aerosol propellant was utilized to create a spray mechanism.

A raw chicken leg was aged at room temperature for several days to ensure high bacterial levels. As shown in FIG. 6, the chicken leg was placed on the surface of a ceramic plate for several seconds (6A), then removed, after which the surface was blotted to remove any trace of chicken juice (6B). Next, the Reichardt's dye solution was sprayed onto the surface using the spray bottle (6C). The test was repeated with an additional piece of chicken to ensure repeatability and gave a similar result.

After spraying the indicator dye solution onto the surface, the entire area that had contained the chicken was decolorized (that is, the indicator spray color changed from blue to very pale or colorless), creating an outline of the chicken (6D). The dye was rapidly de-colorized in the exact spot corresponding to where the chicken had been placed on the surface.

Example 2

Reichardt's Dye in Isopropanol Applied to a Contaminated Surface

Isopropanol was investigated as a carrier which could have additional benefits due to its disinfection capability. Reichardt's dye was dissolved in isopropanol (160 mg dye into 10 mL of isopropanol). Plastic doorknobs were utilized as a "real world" surface on which to test bacterial contamination. Juice from aged chicken was used to mark the surface of one of the knobs. The other door knob was left uncontaminated as a control. Both knobs were wiped to remove traces of contamination. The isopropanol solution of the dye was sprayed on both surfaces. The contaminated area of the doorknob was easily observed by its de-colorization of the Reichardt's dye from blue to colorless.

Example 3

Reichardt's Dye in Isopropanol Indicator Spray Testing for False Positives on Contaminated Surfaces The Reichardt's dye indicator has been shown to have high sensitivity to microbes from chicken. In order to test the indicator for false positives, other components of chicken fluid, such as lipids and proteins, were used. Chicken broth was utilized for its non-bacterial nature and high probability of containing potential interferences.

Swanson® Chicken Broth (Campbell Soup Co., NJ, commercially available from retail grocery stores) from a freshly opened can was pipetted onto a ceramic surface and wiped dry with a SCOTT® paper towel. Juice from aged chicken was also pipette onto the ceramic surface at a different location and wiped dry as a known positive control. The Reichardt's dye indicator (160 mg in 10 ml of isopropanol) was sprayed over the ceramic surface and it was clear that only the side containing the aged chicken juice (and thus bacteria) was de-colorized. From this experiment it can be concluded that, in the case of chicken, it is indeed the bacteria that is triggering the de-colorization response and not some secondary components such as chicken fat or proteins.

Example 4

Reichardt's Dye Indicator Spray as a Cleaning Aid on a Contaminated Surface

The use of Reichardt's dye in isopropanol spray as a cleaning aid was also tested. As shown in FIG. 7, aged chicken juice was applied longitudinally to both halves of a square-shaped ceramic surface (7A). On one half, side A, no cleaning was performed other than vigorously wiping the surface with a SCOTT® paper towel. On the other half, side B, Kimberly-Clark Professional Moisturizing Instant Hand Antiseptic (60% ethanol solution, Roswell Ga.) was applied to the towel and used to clean the surface (7B). The Reichardt's dye spray was then applied to determine if cleaning had a difference (7C). It was clear that although the cleaner had helped, several areas were "missed" (7D). Next, the bottom halves of both striped areas were cleaned vigorously with the K-C Professional Antiseptic again, this time using the cues from the spray to guide where cleaning was most necessary (7E). When the area was sprayed again (7F), no de-colorization took place, verifying the cleanliness of the surface (7G).

Example 5

De-Colorization of Reichardt's Dye-Coated Paper Materials

Figure 8:
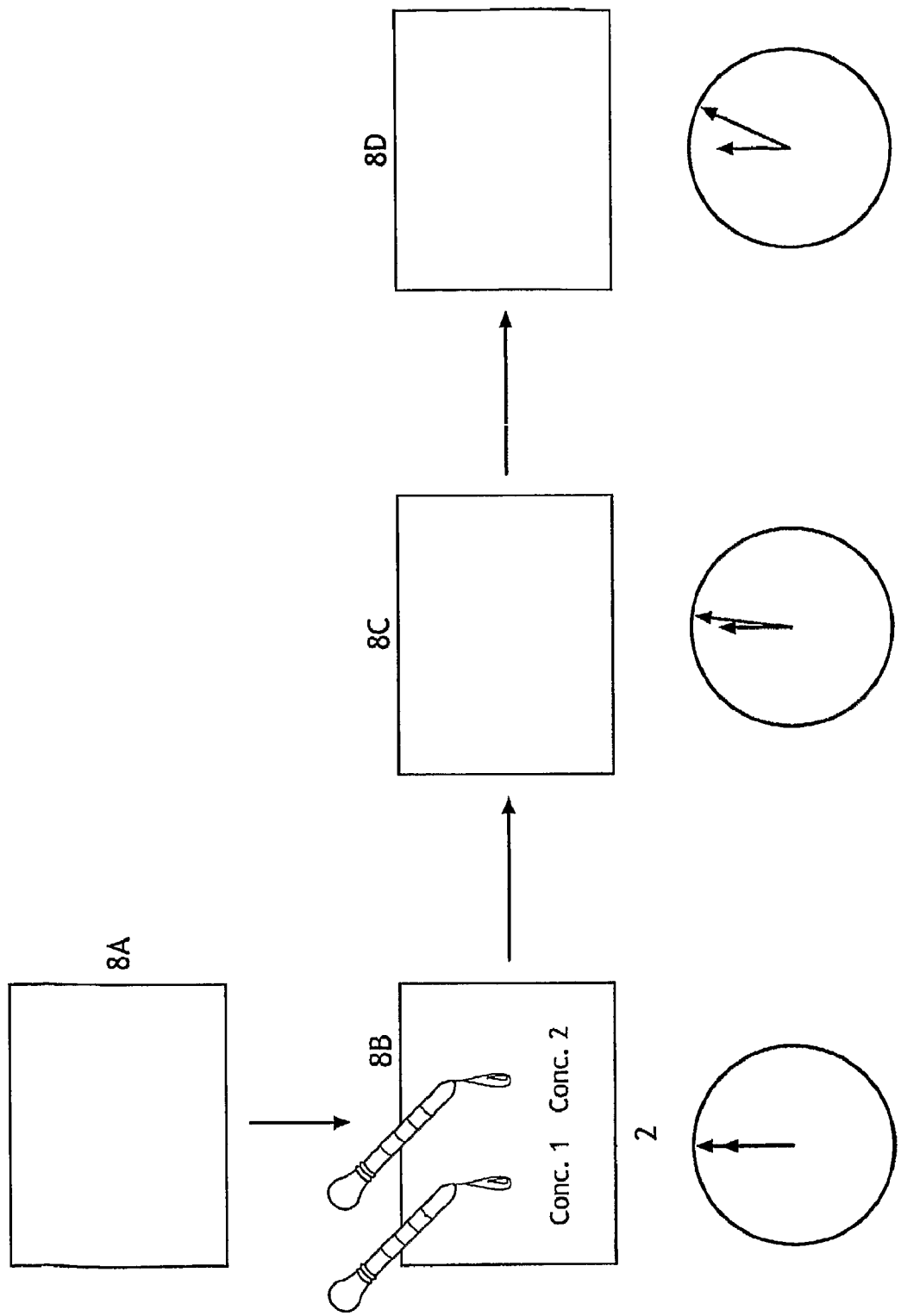
FIGS. 8A-D are diagrams of the indication of microbial contamination using different concentrations of bacteria.

This experiment tested the ability of a surface coating of Reichardt's dye to respond to bacterial contamination. As shown in FIG. 8, a sheet of paper was also brush-coated with a Reichardt's dye solution (80 mg/10 mL acetonitrile) (8A). To this paper was added 100 μL aliquots of $10^7$, $10^6$, $10^5$, and $10^4$ CFU/mL *E. coli* or *S. aureus* solutions (8B). Water was used as a negative control. The dye color was rapidly discharged when contaminated by both types of bacteria (8C), but more rapidly for the *S. aureus* (8D). It was later determined that while both bacteria solutions were indeed at $10^7$ CFU/mL concentrations, the actual concentration of the *S. aureus* solution was $7\times10^7$ CFU/mL compared to $1\times10^7$ CFU/mL for the *E. coli* solution. Water caused slight de-colorization of the dye after several minutes, in contrast to the rapid de-colorization (<1 min) observed for the bacteria solutions.

A sheet of paper self-adhesive stickers (Avery-Dennison) was also brush-coated with two different concentrations of Reichardt's dye solution (160 mg/10 mL acetonitrile, 80 mg/10 mL acetonitrile). The stickers were applied to the lid and latch mechanism of a Huggies® Wet Wipes box. A gloved hand was used to transfer $10^7$ CFU/mL *S. aureus* to the surface of the stickers. Though both concentrations were rapidly de-colorized, the color discharge was more easily visible on the surface which had the lower concentration of dye, indicating that there may be an optimal coating concentration that provides detection and strong visual contrast. The sticker could provide a means for easy and rapid detection of bacterial contamination for a variety of applications.

Example 6

Quantification of Bacteria Concentration Using Reichardt's Dye

Figure 9:
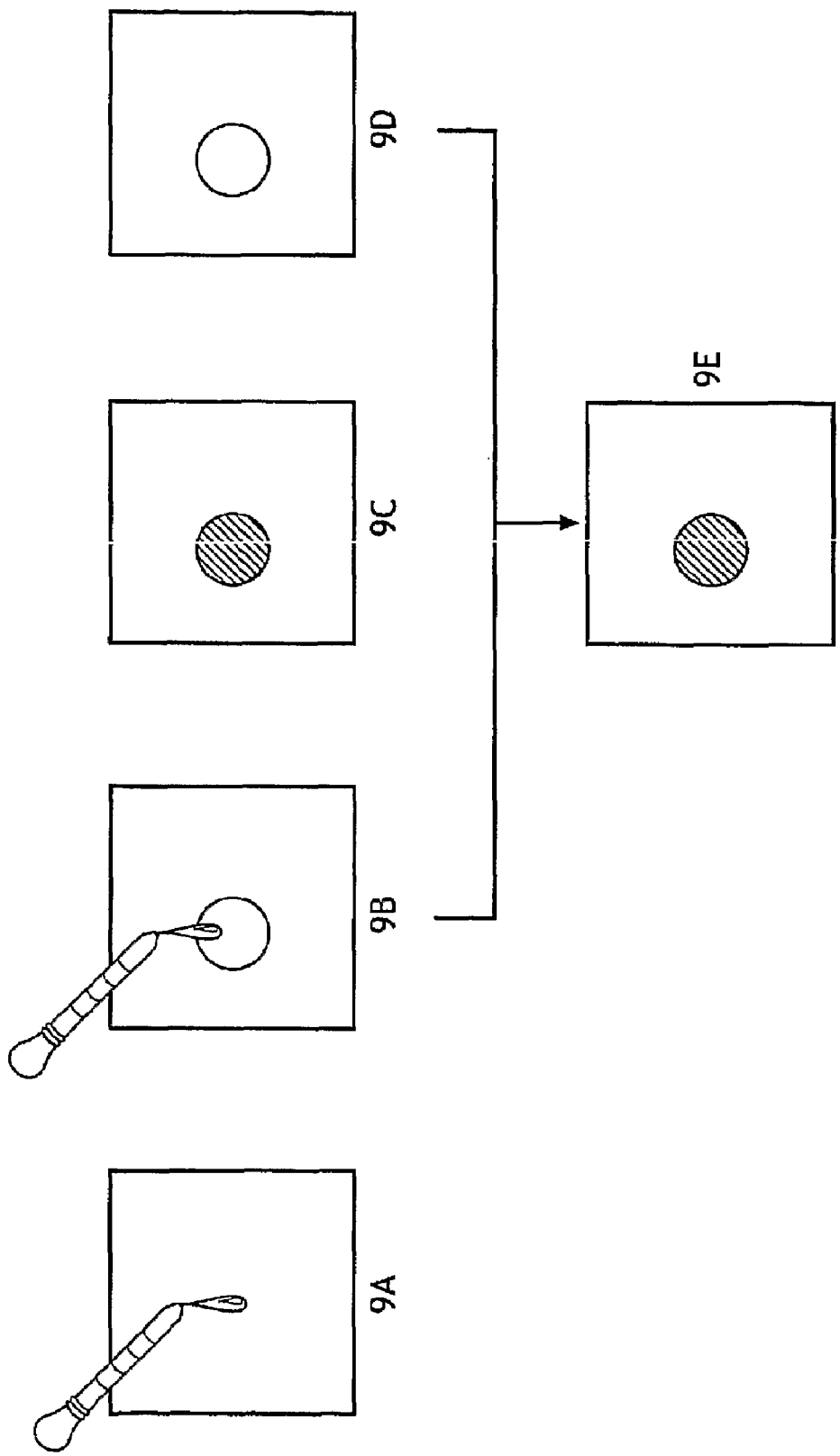
FIGS. 9A-E are diagrams of the indication and quantification of microbial contamination using bacteria and a titration of indicating dye.

A new potential for the Reichardt's dye-based bacterial indicator was realized through testing of liquid dye with bacteria on a substrate rather than substrate-bound dye coming into contact with liquid bacteria (Example 5). This experiment focused on determining how the dye solution responds to known concentrations of bacteria residing on a surface. 100 µl of $10^8$ CFU/ml gram-positive bacteria was placed on a SCOTT® towel (FIG. 9A). To this spot was added a drop of the Reichardt's dye dissolved in acetonitrile (160 mg in 10 ml acetonitrile) (9B).

For comparison, a spot of dye was dried onto the towel and the same amount of bacteria was added. Upon addition to the spot of bacteria, Reichardt's dye was immediately de-colorized. The reaction of bacteria placed onto the dye-containing cellulosic towel, by contrast, takes several minutes to de-colorize. Additional drops of the dye were added to the spot of bacteria (9C), and de-colorization continued until the fourth drop, at which point the purple color persisted (9D). Attempts to restore the dye color on the dye-coated SCOTT® towel by adding acetonitrile using a pipette were unsuccessful (9E).

Example 7

Bacterial Indicator Titration Testing Using Reichardt's Dye

The discovery of rapid de-colorization of the dye solution by substrate-bound bacteria, as well as the fact that the reaction reached an end point, prompted exploration into the ability of the dye to give quantitative information about bacterial CFU/ml. The purpose of this experiment was to titrate various concentrations of substrate-bound bacteria with dye and determine if the amount of dye required to stabilize the color varied at all with bacterial CFU/ml.

On a SCOTT® paper towel was placed 100 µl each of serially diluted *S. aureus* bacterial suspensions. Drops (10 µl) of the Reichardt's dye in acetonitrile solution (40 mg/10 ml) were then pipetted onto each spot where the bacteria was placed. The dye solution was at first colored but was almost instantly (<1 sec) decolorized and additional drops were placed on the same spot until the dye was no longer decolorized and the purple/blue color did not fade. This was repeated on each spot corresponding to where different concentrations of bacteria were placed.

The results showed a good correlation to the level of bacterial contamination on a surface or substrate.

Example 8

Bacteria Titration in Aged Female Urine

To illustrate the practical use of this new method, a sample (100 µl) of aged, pooled female urine was placed on a cellulosic towel to yield several spots each having 100 µl volumes of the urine. Two solutions of the dye were used for a titration study; 40 mg dye/10 ml acetonitrile and 160 mg dye/10 ml acetonitrile. The dye solutions were then placed onto the urine spots in 10 µl aliquots and continued until the blue/purple dye color remained (that is, dye was added to the urine until the color persisted). Table 2 presents the volume of each dye solution required for the dye color to remain steady (that is, no longer decolorized). Aged female urine is known to have high bacterial contamination and this preliminary study shows a high level of contamination in this particular sample.

TABLE 2

| Bacterial Quantification of Female Pooled Urine | | |
|---|---|---|
| SAMPLE | 4 mg/ml Dye Solution | 16 mg/ml Dye Solution |
| Urine | 120 µL | 30 µL |

It is interesting to note that it took four times more dilute (four fold dilution) dye solution than the more concentrated (four fold higher) dye solution. This may allow tailoring of the indicator system for the varying CFU levels seen in different industries (food vs. healthcare, etc) by using maximal dye concentrations to minimize the amount required for saturation. For example, chicken parts may produce anywhere from $10^2$-$10^9$ bacteria levels, depending on time and storage conditions. Food preparers and handlers, however, might only be concerned about levels of bacteria $10^7$ and higher out of concern for illness. Hospitals, on the other hand, are typically treating patients who may already be immune-compromised in some way, either because of disease, illness, or surgery. Hospital staff may therefore be concerned about much lower levels of bacteria than most other industries and could potentially benefit from an indicator dye concentration tailored to their specific needs in order to reduce infection risk to susceptible patients.

Example 9

Testing Bacteria Indicator with a Variety of Microorganisms Including Bacteria, Mold, and Yeast In the same manner as previously described, a cellulosic towel was used as a substrate onto which bacteria and other microorganisms were pipetted. $10^7$ CFU/ml of *S. aureus, C. albicans* (yeast), *G. vaginalis, E. coli P. aeruginosa*, and *L. acidophilus* were pipetted onto the towel (100 µl each). In addition, $10^5$ of *A. niger* (a common mold) was also pipetted onto the towel. Reichardt's dye solution (160 mg in 10 ml of acetonitrile) was then added in 10 µl aliquots to each spot and the numbers of drops needed to establish a persistent color were counted.

The amount of dye required to maintain a persistent purple color for each organism is provided in Table 3. The strongest reaction was observed with *L. acidophilus*, followed by *S. aureus, G. vaginalis, E. coli, P. aeruginosa, C. albicans*, and finally *A. niger*. Although there seemed to be as strong a reaction for the gram-positive *S. aureus* as for the gram-negative *G. vaginalis*

TABLE 3

| Titration of Various Microorganisms with Reichardt's Dye | | |
|---|---|---|
| Compound | Type | Amount of Dye Required for Persistent Color (µl) |
| Lactobacillus | Gram(+) | 110 |
| S. aureus | Gram(+) | 90 |
| G. vaginalis | Gram(−) | 90 |
| E. coli | Gram(−) | 80 |

TABLE 3-continued

Titration of Various Microorganisms with Reichardt's Dye

| Compound | Type | Amount of Dye Required for Persistent Color (µl) |
|---|---|---|
| P. aeruginosa | Gram(−) | 80 |
| C. albicans | yeast | 70 |
| A. niger | Mold | 50 |

Example 10

Testing of Reichardt's Dye Indicator with Bacterial Cell-Wall Components

Insight into how this indicator technology works was obtained by utilizing molecules commonly found in the cell walls of bacteria. Although there is some commonality in the compounds which comprise the surfaces of gram-positive and gram-negative bacteria, their arrangement and chemical composition differ from one another. Gram-negative bacteria have an outer membrane coated with lipopolysaccharide (LPS). LPS lends a net-negative charge to the surface of gram-negative bacteria and contributes to its pathogenesis. Gram-positive bacteria are coated with a thick peptidoglycan, or murein, sheet-like layer. The sheets are formed from alternating N-acetylglucosamine and N-acetylmuramic acid molecules. Teichoic acids are also found in gram-positive bacteria and may be linked to the N-acetylmuramic acid. While gram-negative bacteria also have peptidoglycan, the layer on gram-positive bacteria is much thicker. Furthermore, the peptidoglycan layer of gram-negative bacteria is located underneath the LPS layer, making it less accessible from the surface.

Onto a SCOTT® paper towel were placed solutions of *E. coli*-derived detoxified lipopolysaccharide (Lipid A component removed), lipoteichoic acid derived from *Streptococcus faecalis*, *E. coli*-derived lipopolysaccharide, and muramic acid. With the exception of the pure LPS, all solutions were prepared in 5% (wt/wt), 1% (wt/wt), and 0.2% (wt/wt) concentrations. Pure LPS was prepared in 0.1% (wt/wt), 0.02% (wt/wt), and 0.004% (wt/wt) for safety reasons. Reichardt's dye (160 mg in 10 mL acetonitrile) was added in 10 µl aliquots to each spot and amount of dye required to produce a persistent color was recorded. The reverse experiment was also conducted where the cell-wall compounds were placed onto a spot of dye on the paper towel.

Muramic acid produced the strongest reaction, resulting in a near instantaneous de-colorization of the dye in both experimental set-ups. The other compounds did cause eventual de-colorization of the dye, but did not appear to react as strongly as muramic acid. Because muramic acid is found in greater concentrations on gram-positive bacteria, these results demonstrate the potential of this dye to not only give CFU/mL data, but also the potential to distinguish between gram-positive and gram-negative bacteria based on strength and speed of reaction.

Example 11

Testing of Chicken-Related Components

The Reichardt's dye indicator has been shown to have high sensitivity to microbes growing on raw chicken meat that has been stored at room temperature. With consideration to the potential for false positives, however, it became necessary to test the response of the indicator to other components of chicken fluid, such as lipids and proteins. Canned chicken broth was utilized as a control that would contain chicken derived products such as lipids, protein, etc., to check for potential interferences from these naturally occurring materials.

Freshly opened Swanson® Chicken Broth was pipette onto a hot plate surface and wiped dry with a SCOTT® towel. Juice from raw chicken that had been stored at room temperature for several days was also pipetted onto the hot plate and wiped dry as a positive control. The Reichardt's dye indicator (160 mg in 10 ml of isopropanol) was sprayed over the surface and it was clear that only the side containing the aged chicken juice (and thus bacteria) was de-colorized. From this experiment it can be concluded that, in the case of chicken, it is indeed the presence of microbes that is triggering the de-colorization response and not some other component such as chicken fat or proteins.

Example 12

Effect of Strong Base on Reichardt's Dye De-Colorization

Preliminary results in regard to the interaction of Reichardt's dye with cell wall components such as muramic acid, as well as work directed at identifying potential false positives suggested that a reaction with acids may contribute towards de-colorization of Reichardt's dye. This led to speculation that an acid-base reaction may play a part in the color change observed. An experiment to test the effect of a strong base on decolorized Reichardt's dye was planned.

Several drops of Reichardt's dye (160 mg in 10 ml of acetonitrile) were pipetted onto a SCOTT® towel and allowed to dry. Two compounds known to cause color changes (acetic acid and Aldrich buffer pH 2.0) were each dropped onto two of the spots which led to rapid de-colorization of the dye. A drop of 1 N NaOH was then pipette onto one of each of the spots, causing rapid re-colorization. The blue/purple color of Reichardt's dye returned after the 1 N NaOH was added.

A second experiment was performed using the indicator spray to corroborate these results. Aged raw chicken juice was pipetted onto the hot plate surface in an easily recognizable pattern. The surface was blotted dry and sprayed with Reichardt's dye indicator spray (160 mg in 10 ml acetonitrile), causing de-colorization of the dye in the exact form of the pattern of chicken juice. A drop of 1 N NaOH was then placed on an area that was previously decolorized, leading to re-colorization of that small spot. This was repeated with another area.

To test the possibility that the 1 N NaOH was simply acting on the bacteria and not the dye, aged chicken juice and 1 molar NaOH were mixed in equal proportions and allowed to stand for 30 seconds. This mixture was then used to create another identical (though smaller) pattern. This solution also caused rapid de-colorization of Reichardt's dye, however, the color returned upon addition of 1 N NaOH.

Example 13

Testing of Reichardt's Dye-Coated Stickers with Normal and Bacterial Vaginosis (BV)-Infected Vaginal Fluid Considering the high prevalence of vaginal infections of bacterial origin, an experiment was performed to determine the response of Reichardt's dye-coated stickers to healthy (low pH, no bacterial infection), a pH positive/BV negative (no bacterial infection, but higher than normal pH), and pH positive/BV positive (higher than normal pH and known bacterial infection) vaginal fluid samples. A sheet of stickers was brush-coated with two different concentrations of Reichardt's dye solution (160 mg/10 mL acetonitrile, 80 mg/10 mL acetonitrile, 40 mg/10 mL acetonitrile, 20 mg/10 mL acetonitrile). A sticker of each concentration was tested with normal, BV positive/pH positive, and BV negative/pH positive vaginal fluid samples.

Normal vaginal fluid yielded the sharpest de-colorization of the dye, presumably due to the combination of lactobacillus and low pH. The BV positive/pH positive sample exhibited the next sharpest de-colorization, perhaps due to the presence of large numbers of BV bacteria. The BV negative/pH positive sample only faintly de-colorized the dye, perhaps due to a lesser amount of lactobacillus than in the normal sample. The three states of de-colorization were easily distinguishable, suggesting that there may be a diagnostic potential for this technology within the vaginal health field.

Example 14

Testing of Common Surface with Reichardt's Dye Indicator Spray

It is well known that bacteria can survive on dry surfaces for hours, if not days. The ability to identify bacteria and other microbes on common surfaces and alert consumers or workers to contamination would aid in cleaning and disinfection and help minimize the spread of infection.

Figure 10:
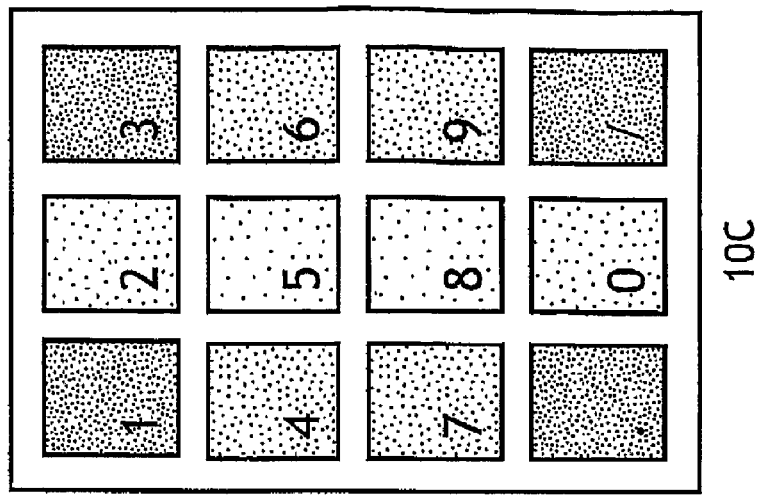
FIGS. 10A-C are diagrams of the indication of microbial contamination on a computer keyboard.
Figure 10:
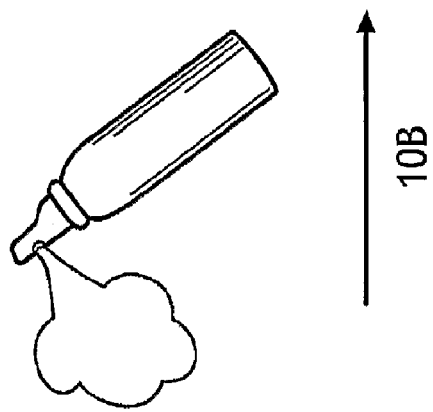
Figure 10:
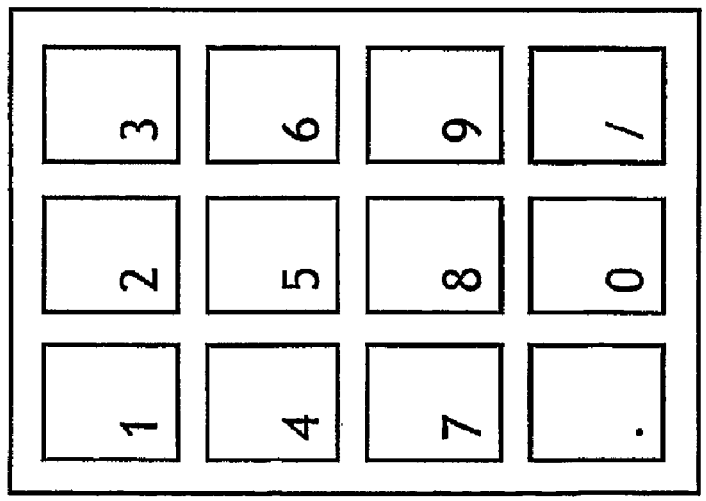

As shown in FIG. 10, an old computer keyboard was used as a model "real-world" surface to test the microbial indicator spray (10A). Reichardt's dye was dissolved in isopropanol (160 mg in 10 mL of isopropanol) and attached to an aerosol-based spray device. The keyboard was then sprayed with the indicator solution (10B).

Spraying of the keyboard with the Reichardt's dye indicator solution caused rapid de-colorization of the dye in certain areas (10C). It is interesting that only certain keys or areas showed contamination, allowing for specific identification of keys that are highly sullied, such as the number pad. As keyboards are used quite often, but rarely cleaned, this surface indeed provides a glimpse of microbial levels on real-world surfaces.

Example 15

Use of a Surfactant to Enhance Sensitivity of the Bacterial Indicator

Figure 11:
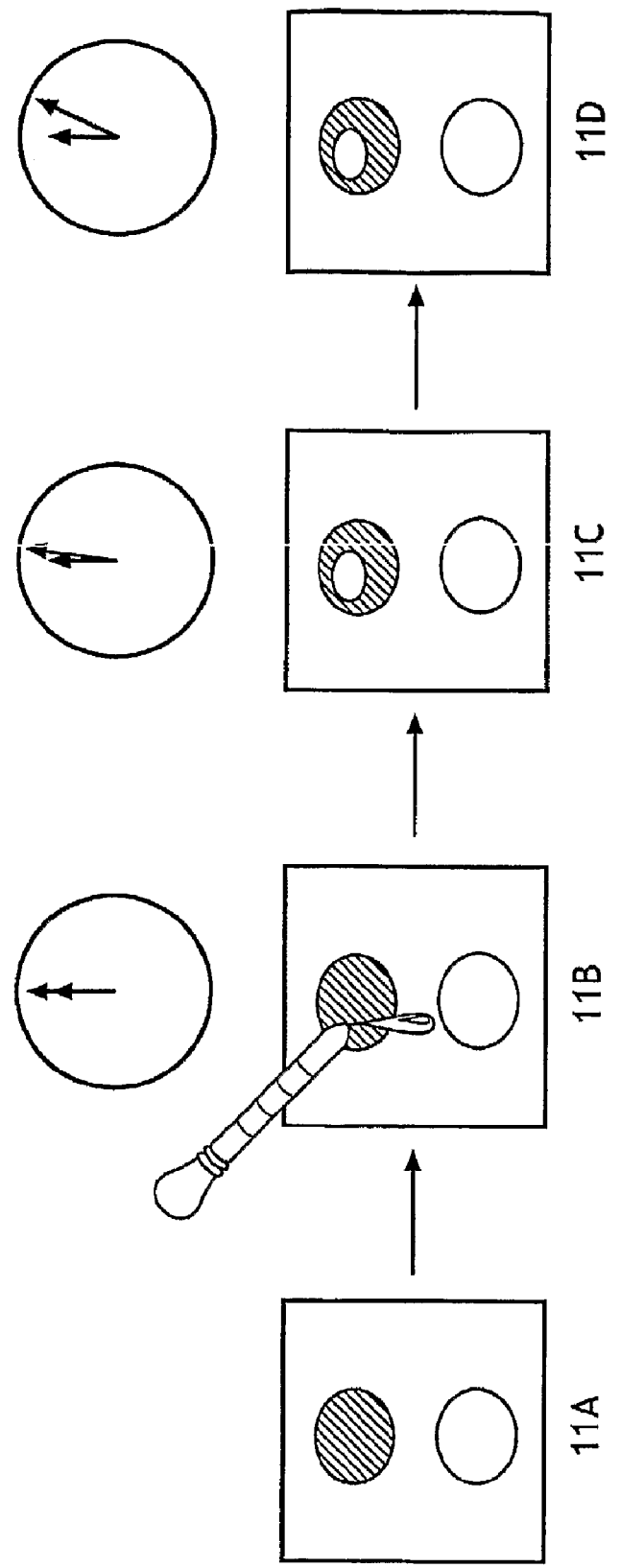
FIGS. 11A-D are diagrams of the indication of microbial contamination with and without surfactant in the solution.

A solution of Reichardt's dye (80 mg/110 mL acetonitrile) and TWEEN® 80 (200 μL) polyoxyethylene surfactant (from Fischer Scientific, Pittsburgh, Pa.) was prepared. This solution was then used to coat a ceramic surface (FIG. 11) and allowed to air dry. A second solution of Reichardt's dye (80 mg/10 mL acetonitrile) without surfactant was placed on the surface and allowed to air dry as well (11A). After drying, a drop of aged chicken juice known to have a high bacterial count was placed on the each coating area (11B). The area containing the TWEEN® 80 surfactant (11C) de-colorized at a much faster rate (>20-30 seconds) when compared to the area that did not contain the TWEEN® surfactant (11D). Furthermore, the addition of TWEEN® surfactant allowed for easy removal of the dye from the surface. The addition of a small amount of water allowed for complete removal from the surface while the addition of water to the spot that did not contain the surfactant did not improve ease of removal from the surface.

Example 16

Importance of Solvent Choice

The behavior of Reichardt's dye coatings made using various different solvents was evaluated.

Figure 12:
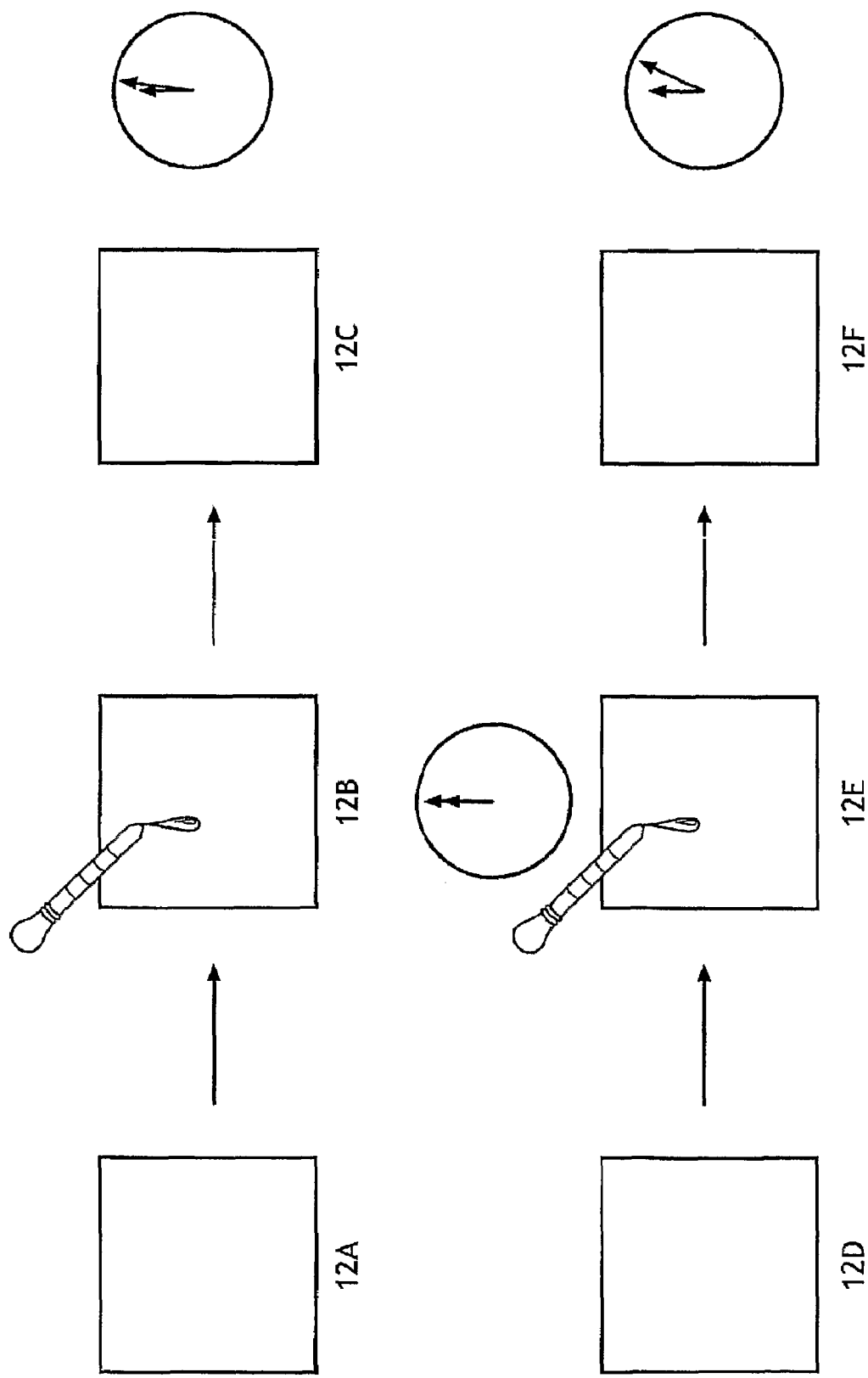
FIGS. 12A-F are diagrams of the indication of the speed of indication of microbial contamination depending on the solvent.

Solutions of Reichardt's dye in acetonitrile, isopropanol, and xylenes were prepared and the solutions were used to coat SCOTT® kitchen rolls towels and allowed to air-dry (FIGS. 12A and 12D). The treated towels had 100 μl aliquots of *S. aureus* placed on them (12B,E) and the coating was observed for a color change. Only the acetonitrile solution-based coating had a rapid de-colorization where the bacterial suspension was placed (12C). The Reichardt's dye was observed to have an even color when dissolved in acetonitrile. No visible color change was observed with the other two solvent coatings (12F).

The inventors found that the concentration of Reichardt's dye could be adjusted such that isopropanol could be utilized as a solvent for the dye. Though the color of the dye is less intense than that seen with acetonitrile, the decolorization in response to microbial contamination is readily and easily observed.

Example 17

N-docosyl-merocyanine Dye Coated onto Cotton Fabric

The transparent film covering half of a fresh chicken on a polystyrene tray (from supermarket) was stored at room temperature for three weeks. The pale yellow juices that collected in the polystyrene tray were collected using a pipette and used for tests.

47 mg of 1-docosyl-4-(4-hydroxystyryl)-pyridinium bromide (from Aldrich Chemical) was mixed with 10 g dimethylformamide. A small amount of solids remained after shaking and allowing to settle. The orange supernatant fluid was dropped onto woven cotton fabric of basis weight (29.2 cm×20.3 cm=6.888 g) to make orange-yellow colored circles. One drop of 1N sodium hydroxide solution was added to one orange-yellow spot on the cotton fabric, changing the color from orange-yellow to a pinkish orange.

Aged chicken juice was spotted onto the orange-yellow spots on the cotton fabric, producing a color change to very pale yellow. The color change was rapid on cotton. Similarly, aged chicken juice was dropped onto the pinkish-orange areas on the cotton (dye+NaOH soln.) causing a similar color change from pinkish-orange to very pale yellow.

Example 18

N-methylmerocyanine Coated onto Kitchen Paper Towel & Aged Urine

Female human urine was collected and stored in a glass jar at room temperature for 8 days. N-methyl merocyanine dye of the following structure was synthesized as described above. 0.5 g was dissolved in 20 ml deionized water and coated onto a SCOTT® kitchen roll paper towel by dipping the towel into the solution, allowing the excess to drip off, and then allowing the coated toweling to dry at ambient conditions. The paper towel was stained a deep orange color by the dye.

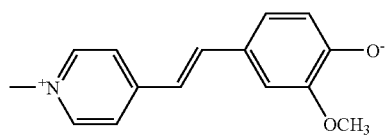

Aged urine was dropped onto the orange colored towel to give an immediate color change from deep orange to pale yellow. As a control, the aged urine was filtered through a 0.2 micron filter to remove bacteria and other microbes. After filtration, the aged urine did not cause a color change when dropped onto the towel suggesting that microbes were responsible for causing the color change vs. other components in the aged urine.

Example 19

N-methylmerocyanine Coated onto Kitchen Toweling & Aged Urine

Female human urine was collected and stored for 24 hours at 37° C. Pooled female urine may be expected to have a bacterial loading of approximately $1\times10^5$ CFU/ml after storage under these conditions. N-methyl merocyanine dye of the following structure 26 was synthesized as described above. 0.5 g was dissolved in 20 ml deionized water and coated onto a SCOTT® kitchen roll paper towel by dipping the towel into the solution, allowing the excess to drip off, and then allowing the coated toweling to dry at ambient conditions. The paper towel was stained a deep orange color by the dye.

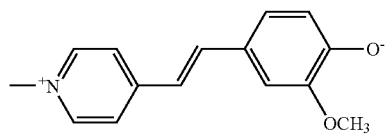

26

The aged urine was dropped onto the orange colored towel to give an immediate color change from deep orange to pale yellow. As a control, the aged urine was filtered through a 0.2 micron filter to remove bacteria and other microbes. After filtration, the aged urine did not cause a color change when dropped onto the towel suggesting that microbes were responsible for causing the color change vs. other components in the aged urine.

Example 20

Figure 13:
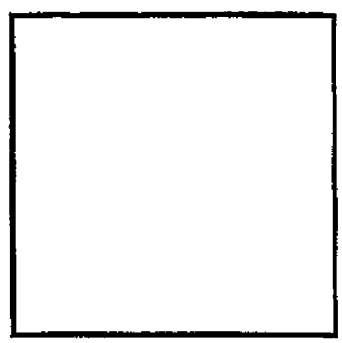
FIGS. 13A-C are diagrams of the indication of microbial contamination where the colorant is dried onto a substrate.
Figure 13:
Figure 13:
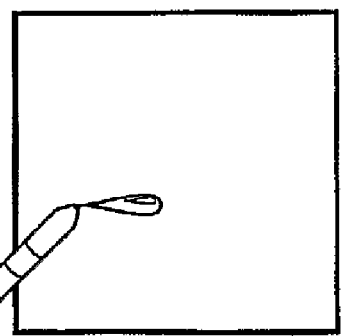
Figure 13:
Figure 13:
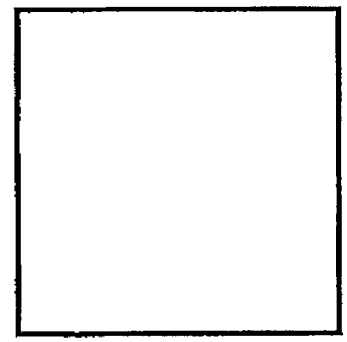

N-methyl merocyanine Dye Coated onto Kitchen Paper Towels and Pet Bird Bowel Movements Budgerigar feces was collected from a caged pet budgie, and shaken in approximately 10 ml of Atlanta city domestic tap water. N-methyl merocyanine dye of structure 26 above was synthesized as described above. 0.5 g was dissolved in 20 ml deionized water and coated onto a SCOTT® kitchen roll paper towel by dipping the towel into the solution, allowing the excess to drip off, and then allowing the coated toweling to dry at ambient conditions. The paper towel was stained a deep orange color by the dye (FIG. 13A).

Drops of the budgie feces suspension in tap water were spotted onto the coated towel (13B) and produced an immediate color change from deep orange to pale yellow where the suspension was added (13 C). As a control, Atlanta city domestic tap water was dropped onto a different area of the towel and while the color was diluted somewhat by the water, the area remained orange.

Example 21 (Prophetic)

Indicator Dyes Used in a Coating 1 gram of hydroxypropyl methyl cellulose, 0.5 gram N-methyl merocyanine of structure 26 may be dissolved in a mixture of 10 grams of water and 10 grams of isopropyl alcohol with good stirring. This solution may be coated onto polyester film and allowed to dry at room temperature to produce a coated flexible film capable of detecting the presence of microbes.

Example 22 (Prophetic)

Indicator Dyes in a Coating 1 g of ethylcellulose, 0.25 g N-methyl merocyanine of structure 26 may be dissolved in 20 grams of tetrahydrofuran. This solution may be coated onto polyester film and allowed to dry at room temperature to produce a coated flexible film capable of detecting the presence of microbes.

Example 23

Lateral Flow Device

Millipore nitrocellulose HF75 membrane (from Millipore Corporation of Billerica, Mass., USA) was laminated onto a plastic supporting card (from Millipore Corp.) having a length of approximately 30 centimeters. On both the detection zone and control zone, a solution of 5 weight percent Reichardt's dye in iso-propanol was hand striped. The membrane was dried in a laboratory oven for 1 hour at a temperature of 37.5° C. After the membrane card was taken from the oven, a cellulosic wicking pad (Cat# CFSP203000 from Millipore Corp.) was attached to one end of the membrane closer to the control zone. The other end of the card, used to attach the sample pad, was cut off. The card was then sliced into 4 mm strips to form half sticks.

Once the half sticks were prepared, a bacteria solution was applied to the end of the detection membrane. Capillary action pulled the solution and bacteria into the detection zone and a color change was noted in the detection zone. The control line color remained the same through out the test.

Example 24

Cyclodextrin Enhancement

A SCOTT® paper towel was first coated with hydroxypropyl-beta-cyclodextrin (from Cerestar International, Hammond, Ind., USA) in solution in water (1 gram in 20 ml) by dipping and air-drying at ambient temperature. When dry the coated paper towel was treated with a solution of Reichardt's dye in isopropanol (1 weight percent) and allowed to air-dry. The dried towel was a purple/blue in color. Here the cyclodextrin hinders the crystallization of the dye allowing a more vivid color of the dye to occur on the paper towel. This coated towel was used in a test with gram-negative bacteria (*E. Coli*) and found to turn colorless in less than 5 seconds when an aliquot of 100 microliters of media containing 10,000 CFU/ml was applied to the towel. This decolorization was found to occur down to the bacteria concentration of 500 CFU/ml, though this took as long as 15 seconds. Thus by hindering the dye from crystallizing, the dye is believed to be present on the substrate as single molecules and therefore the sensitivity of the dye to bacteria levels increases. The inventors believe that by careful use of a coating (e.g. cyclodextrin) on the towel a mono-molecular coating of dye will occur on the surface of the substrate and maximum sensitivity will occur.

Example 25

Dry Sample Testing

A test using the Reichardt's dye coated paper towel with a "dry" bacteria sample, not in solution was carried out. A dry sample of a colony of *E. Coli* bacteria lifted off an agar petri dish containing a series of growing cultures was used. This dry sample was then rubbed onto a pre-moistened dye coated SCOTT® paper towel. The area where the colony was placed and rubbed turned colorless within 1-5 seconds. This is a similar to how a wet wipe towel would be used and it performed well.

Example 26

Bleach Indicator Test

A mixture of Reichardt's Dye and 3,3',5,5'-tetramethylbenzidine (TMB) was coated onto a SCOTT® paper towel and allowed to air-dry. A dilute bleach solution was applied to the paper towel which resulted in the Reichardt's dye decolorizing and the TMB turning orange/yellow color. This shows that a bleach indicator can be built into a bacteria indicating wiper.

In the final test, a SCOTT® paper towel having a coating of Reichardt's dye and TMB chemistries was exposed to suspension of *E. Coli* bacteria drop-wise. The towel area that came in contact with the bacteria decolorized to a white spot in less than 10 seconds. No orange/yellow color was observed to develop.

Example 27

UV-Vis Absorption Spectra of Merocyanine and Zwitterionic Dyes

Reichardt's dye was used without further purification. N-n-hexyl and N-n-dodecyl merocyanine dyes were synthesized as described. Solvents used were obtained from Aldrich Chemical and were HPLC grade. A Shimadzu UV-1601 UV-Visible Spectrophotometer (Shimadzu Corporation) was used to measure the longest wavelength peak absorption of the dyes in the range of 400 to 800 nm, dissolved in three different solvents, contained in quartz curvettes. The following table contains the results of the testing with the solvents on the left side and dyes across the top.

|  | Hexyl Merocyanine | Dodecyl merocyanine | Reichardt's dye |
| --- | --- | --- | --- |
| Acetone | 617.5 nm (Green) | 617 nm (Green) | 674 nm (bluish green) |
| Methanol | 514 nm (Orange) | 522 nm (Orange) | 509 nm (red) |
| Acetonitrile | 582 nm (Greenish-blue) | 600 nm (Blue) | 623 nm (Blue) |

The merocyanine dyes also showed absorption near 400 nm, in addition to the longer wavelength absorption, which altered the perceived color.

Clearly, based upon the spectroscopic measurements, these dyes show large shifts (>10 nm) in maximum wavelength peak absorption between these microbe detecting dyes when dissolved in different solvents.

Example 28

Testing of Indicator with Viruses

Virus testing was carried out by Gibraltar Laboratories (Fairfield, N.J.) under the direction and supervision of one of the inventors. Polio virus type 1 and Rhinovirus were prepared and inoculated into MA-104 embryonic monkey kidney cells propagated and fed with Dulbecco's Modified Eagle's Medium (DMEM), supplemented with fetal calf serum to a concentration of 5% and incubated at 37° C.±1° C. in its presence of 5% $CO_2$ for 6 days. Viral propagation was detected by microscopic observation of infected cell sheets for cellular disintegration (cytopathic effect, CPE) such as rounding, crenation, lysis, pyknosis, etc. as observed in at least 50% of the cell sheet. Cytotoxicity was measured as the extent of cellular disintegration as produced by the agent alone without the virus. Virus was titrated using ten-fold serial dilutions in DMEM, 4 replicates MA 104 cultures per dilution, each replicate inoculated with 0.1 mL of virus dilution. The extent of viral replication was calculated as the tissue culture infectious dose-50% (TCID 50) as determined by the method of Reed and Muench.

Reichardt's dye-coated stickers (160 mg/10 mL acetonitrile, 80 mg/10 mL acetonitrile, 40 mg/10 mL acetonitrile, and 20 mg/10 mL acetonitirile) were used as a test surface. 50 µl of undiluted virus ($10^{-10}$/50 µl for Polio virus and $10^{-9}$/50 µl for Rhinovirus) in media was dropped onto each sticker and allowed to stand for five minutes before removing the droplet with a cotton swab. Aliquots of media alone, virus-free cell culture media, and virus-free cell culture saline were utilized as control samples and also allowed to stand for five minutes before swabbing. For poliovirus, the saline control appeared to interfere with technology, while the media did not cause de-colorization. Dilutions of Polio virus in media were therefore used for the remainder of the experiment. The virus was diluted serially in media in ten-fold increments and 50 µl aliquots applied to each sticker. After allowing to stand for five minutes, the droplets were swabbed off the sticker. For Rhinovirus, the media control was found to interfere while the saline control did not lead to de-colorization of the dye. Thus, ten-fold serial dilutions of the virus diluted in saline were applied to the stickers in 50 µl aliquots and swabbed after five minutes. For both Polio virus and Rhinovirus, the stickers were de-colorized down to $10^{-6}$ (i.e. the sixth in the series of ten-fold dilutions), indicating that the dye-coated stickers possess sensitivity towards the detection of these viruses.

Two solutions of Reichardt's dye (80 mg/10 mL acetonitrile with or without 400 µl TWEEN 80 surfactant) were prepared. A 100 µl drop of either Polio virus or Rhinovirus (both undiluted in media) was pipetted onto a folded Scott towel and drops of the Reichardt's dye were added to each of the virus-containing spots. The color was rapidly discharged for both surfactant- and non-surfactant-containing solutions. Dye was eventually added until the color persisted (approximately 9 drops). The same media and saline controls mentioned previously were also tested. Though media did exhibit some ability to de-colorize the dye, the saline presented the same titration behavior previously observed with water.

Comparative Examples (Not Examples of the Invention)

Aged chicken was used as a bacteria source for comparative examples. The transparent film covering half of a fresh chicken on a polystyrene tray (from supermarket) was stored at room temperature for three weeks. The pale yellow juices that collected in the polystyrene tray were collected using a pipette and used for tests.

Comparative Example 1

Aged chicken juice was dropped onto a SCOTT® paper towel. Cl Acid Green 41 (from Aldrich Chemical) solution (0.008 mol/l) (an example of an hydroxyanthraquinone dye) structure 27 below was dropped onto the aged chicken juice. No color changes were observed. As a control, 100 mg of Reichardt's dye was suspended in 10 ml acetonitrile. This suspension was dropped onto the aged chick juice and immediately decolorized.

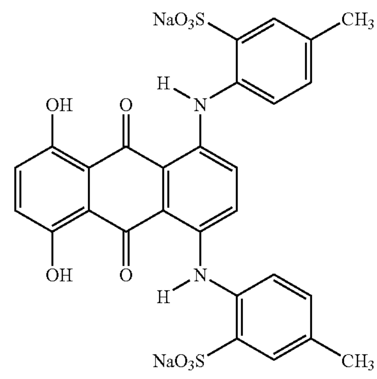

27

Comparative Example 2

Aged chicken juice was dropped onto a SCOTT® paper towel. Cl Acid Green 25 solution (0.008 mol/), structure 28 below, an example of an anthraquinone dye, was dropped onto the aged chicken juice. No color changes were observed. As a control, 100 mg of Reichardt's dye was suspended in 10 ml acetonitrile. This suspension was dropped onto the aged chick juice and immediately decolorized.

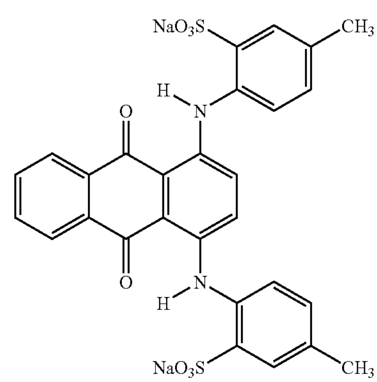

28

Comparative Example 3

Aged chicken juice was dropped onto a SCOTT® paper towel. 50 mg of Cl Acid Red 37 (from Aldrich Chemical), structure 29 below and example of an aminoazo dye, was dissolved in 10 ml deionized water. This dye solution was dropped onto the aged chicken juice on the paper towel. No color changes were observed. As a control, 100 mg of Reichardt's dye was suspended in 10 ml acetonitrile. This suspension was dropped onto the aged chick juice and immediately decolorized.

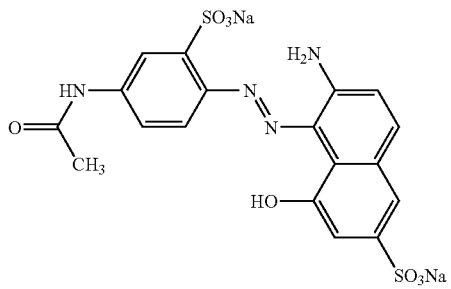

29

Comparative Example 4

Aged chicken juice was dropped onto a SCOTT® paper towel. 50 mg of Cl Acid Yellow 23 (also known as the food colorant tartrazine) (from Aldrich Chemical), structure 30 below, and example of a phenylpyrazolone dye, was dissolved in 10 ml deionized water. This dye solution was dropped onto the aged chicken juice on the paper towel. No color changes were observed. As a control, 100 mg of Reichardt's dye was suspended in 10 ml acetonitrile. This suspension was dropped onto the aged chick juice and immediately decolorized.

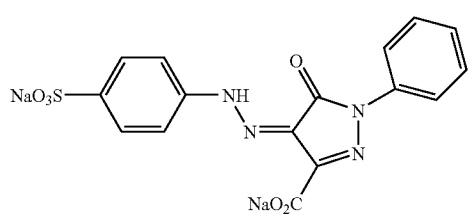

30

Comparative Example 5

Aged chicken juice was dropped onto a SCOTT® paper towel. Cl Acid Red 52 (sulforhodamine B), structure 31 below, an example of a xanthene dye, solution in water was dropped onto the aged chicken juice on the paper towel. No color changes were observed. As a control, 100 mg of Reichardt's dye was suspended in 10 ml acetonitrile. This suspension was dropped onto the aged chick juice and immediately decolorized.

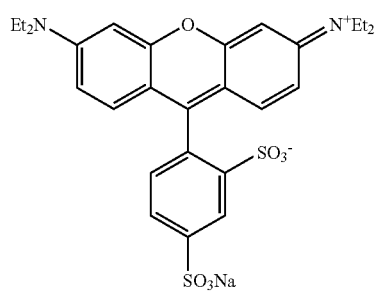

31

Comparative Example 6

Aged chicken juice was dropped onto a SCOTT® paper towel. 30 mg of Cl Acid Blue 74 (also known as Indigo Carmine), structure 32 below, (from Aldrich Chemical), as an example of an indigoid dye, was dissolved in 10 ml deionized water. This dye solution was dropped onto the aged chicken juice on the paper towel. No color changes were observed. As a control, 100 mg of Reichardt's dye was suspended in 10 ml acetonitrile. This suspension was dropped onto the aged chick juice and immediately decolorized.

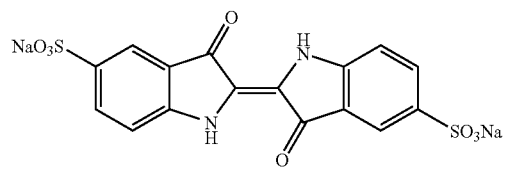

32

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A substrate that contains fibers, wherein the substrate is coated with a composition comprising a zwitterionic microbe-sensitive colorant that undergoes a visually detectable color change in the presence of bacteria.

2. The substrate of claim 1, wherein the composition comprises a mobile phase.

3. The substrate of claim 2, wherein the mobile phase includes a liquid.

4. The substrate of claim 2, wherein the mobile phase includes a gel.

5. The substrate of claim 1, wherein the colorant is Reichardt's dye.

6. The substrate of claim 1, wherein the colorant has the general structure:

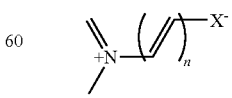

wherein,
n is 0 or greater; and
X is oxygen, carbon, nitrogen, phosphorous or sulfur.

7. The substrate of claim 1, wherein the colorant has the general structure:

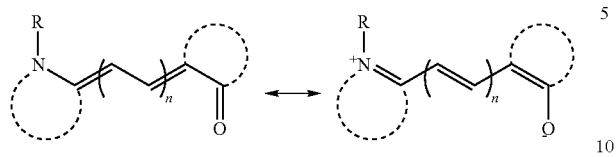

wherein, n is 0 or greater; and

R is alkyl, aryl, or phenyl.

8. The substrate of claim 1, wherein the colorant is selected one of the following structures:

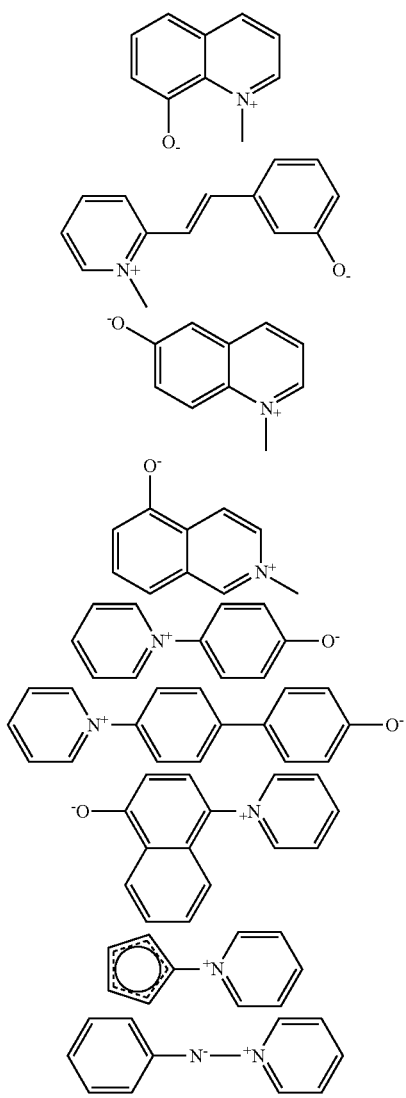

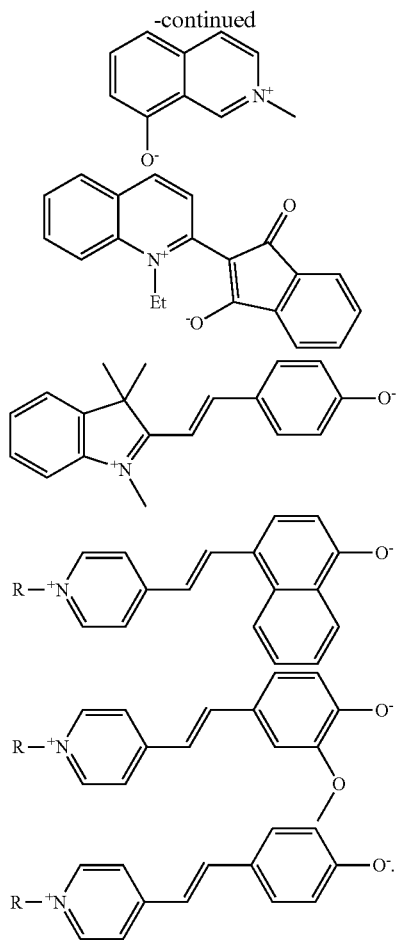

9. The substrate of claim 1, wherein the composition is present in an amount from about 0.01 to about 10 weight percent on a dry basis.

10. The substrate of claim 1, wherein the composition is present in an amount of from about 0.05 to about 5 weight percent on a dry basis.

11. The substrate of claim 1, wherein the fibers include meltblown fibers, spunbonded fibers, or a combination thereof.

12. The substrate of claim 1, wherein the fibers include cellulosic fibers.

13. The substrate of claim 1, wherein the fibers include staple fibers.

14. The substrate of claim 1, wherein the color change occurs in less than one minute after exposure to the bacteria.

15. The substrate of claim 1, wherein the colorant changes color at a rate proportional to the concentration of the bacteria.

16. The substrate of claim 1, wherein the bacteria are gram negative bacteria.

17. The substrate of claim 1, wherein the bacteria are gram positive bacteria.

* * * * *